United States Patent [19]

Pineiro

[11] Patent Number: 5,194,440
[45] Date of Patent: Mar. 16, 1993

[54] SUBSTITUTED CYCLIC SULPHAMIDE DERIVATIVES

[75] Inventor: Jose L. C. Pineiro, Harlow, England

[73] Assignee: Merck Sharp & Dohme Ltd., Hertsfordshire, England

[21] Appl. No.: 839,660

[22] Filed: Feb. 20, 1992

[30] Foreign Application Priority Data

Feb. 27, 1991 [GB] United Kingdom ............... 9104136

[51] Int. Cl.$^5$ ............... A61K 31/445; C07D 417/02; C07D 285/16; C07D 285/10

[52] U.S. Cl. ............... 514/320; 514/321; 514/322; 514/323; 514/324; 514/362; 544/8; 546/209; 546/271; 546/273; 546/274; 546/280; 548/134

[58] Field of Search ............... 548/134; 514/362, 320, 514/321, 322, 323, 324; 546/280, 209, 271, 273, 274; 544/8

[56] References Cited

U.S. PATENT DOCUMENTS 4,692,531 9/1987 Algieri et al. ............... 548/134

FOREIGN PATENT DOCUMENTS 0313397 4/1989 European Pat. Off. ............ 548/134
2083463 3/1982 United Kingdom ............... 548/134

OTHER PUBLICATIONS

A. Doenicke, et al The Lancet, 1988, 1, 1309–11.
Design of Prodrugs, ed. H. Bundgaard, Elsevier, 1985.
Indian J. Chem., 1982, 21B, 941.
Chem. Ber., 1978, 111, 1915.
Protective Groups in Organic Chemistry, ed. J. F. W. McOmie, Plenum Press, 1973.
Protective Groups in Organic Synthesis, John Wiley & Sons, 1981.
J. Neurosci., 1987, 7, 894.
Arch. Pharm., 1990, 342, 111.
J. Org. Chem., 1982, 47 536.

Primary Examiner—Mary C. Lee
Assistant Examiner—Jospeh K. McKane
Attorney, Agent, or Firm—Manfred Polk; Charles M. Caruso

[57] ABSTRACT

A class of substituted cyclic sulphamide derivatives are selective agonists of 5-HT$_1$-like receptors and are therefore useful in the treatment of clinical conditions, in particular migraine and associated disorders, for which a selective agonist of these receptors is indicated.

8 Claims, No Drawings

SUBSTITUTED CYCLIC SULPHAMIDE DERIVATIVES

The present invention relates to a class of substituted cyclic sulphamide derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

5-HT$_1$-like receptor agonists which exhibit selective vasoconstrictor activity have recently been described as being of use in the treatment of migraine (see, for example, A. Doenicke et al., *The Lancet*, 1988, Vol. 1, 1309-11). The compounds of the present invention, being selective 5-HT$_1$-like receptor agonists, are accordingly of particular use in the treatment of migraine and associated conditions, e.g. cluster headache, chronic paroxysmal hemicrania, headache associated with vascular disorders, tension headache and paediatric migraine.

EP-A-0313397 describes a class of tryptamine derivatives substituted by a five-membered heteroaliphatic ring, which are stated to be specific to a particular type of "5-HT$_1$-like" receptor and thus to be effective therapeutic agents for the treatment of clinical conditions, particularly migraine, requiring this activity. GB-A-2083463 describes a class of inter alia tryptamine derivatives substituted by an aminosulphonylamino or aminosulphonylaminoalkyl moiety, which compounds are stated to be potentially useful for the treatment of migraine. However, neither of these publications discloses or suggests the substituted cyclic sulphamide derivatives provided by the present invention.

The present invention provides a compound of formula I, or a salt or prodrug thereof:

$$A^1\text{-N}(A^2)\text{-S(O)}_2\text{-N}(A^3)\text{-E-F} \quad \text{(I)}$$

(with X bridging the two nitrogens)

wherein

—X— represents —(CH$_2$)$_m$— in which m is 2 or 3;
A$^1$ represents hydrogen, hydrocarbon or a heterocyclic group;
A$^2$ and A$^3$ independently represent hydrogen or C$_{1-6}$ alkyl;
E represents a bond or a straight or branched alkylene chain containing from 1 to 4 carbon atoms; and
F represents a group of formula

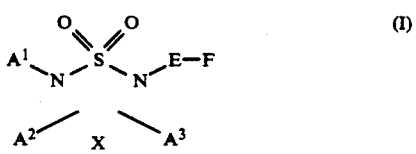

in which
U represents nitrogen or C—R$^2$;
V represents oxygen, sulphur or N—R$^3$;
R$^1$ represents —(CH$_2$)$_p$CHR$^4$.NR$^6$R$^7$ or a group of formula

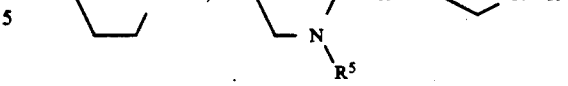

in which the broken line represents an optional chemical bond;
p is 1 or 2; and
R$^2$, R$^3$, R$^4$, R$^5$, R$^6$ and R$^7$ independently represent hydrogen or C$_{1-6}$ alkyl.

For use in medicine, the salts of the compounds of formula I will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable non-toxic acid such as hydrochloric acid, fumaric acid, maleic acid, succinic acid, acetic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include C$_{1-6}$ alkyl, C$_{2-6}$ alkenyl, C$_{2-6}$ alkynyl, C$_{3-7}$ cycloalkyl, C$_{3-7}$ cycloalkyl(C$_{1-6}$)alkyl, aryl and aryl(C$_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include C$_{3-7}$ heterocycloalkyl, C$_{3-7}$ heterocycloalkyl(C$_{1-6}$)alkyl, heteroaryl and heteroaryl(C$_{1-6}$)alkyl groups.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl, isopropyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl, cyclobutyl, cyclopentyl and cyclohexyl.

A particular aryl group is phenyl.

Particular aryl($C_{1-6}$)alkyl groups include benzyl, phenethyl and phenylpropyl.

Suitable heterocycloalkyl groups include azetidinyl, pyrrolidyl, piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, imidazolyl, oxadiazolyl and thiadiazolyl groups.

A particular heteroaryl($C_{1-6}$)alkyl group is pyridylmethyl.

The hydrocarbon and heterocyclic groups may in turn be optionally substituted by one or more groups selected from $C_{1-6}$ alkyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, $-NR^vR^w$, $-NR^vCOR^w$, $-NR^vCO_2R^w$, $-NR^vSO_2R^w$, $-CH_2NR^vSO_2R^w$, $-NHCONR^vR^w$, $-CONR^vR^w$, $-SO_2NR^vR^w$ and $-CH_2SO_2NR^vR^w$, in which $R^v$ and $R^w$ independently represent hydrogen, $C_{1-6}$ alkyl, aryl or aryl($C_{1-6}$)alkyl, or $R^v$ and $R^w$ together represent a $C_{2-6}$ alkylene group.

When $R^v$ and $R^w$ together represent a $C_{2-6}$ alkylene group, this group may be an ethylene, propylene, butylene, pentamethylene or hexamethylene group, preferably butylene or pentamethylene.

The term "halogen" as used herein includes fluorine, chlorine, bromine and iodine, especially fluorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

The alkylene chain E may be, for example, methylene, ethylene, 1-methylethylene, propylene or 2-methylpropylene. Alternatively, the group E may represent a single bond such that the group F in formula I is attached directly to the cyclic sulphamide moiety.

The group F is suitably an indole, benzofuran or benzthiophene moiety of formula FA, or an indazole moiety of formula FB:

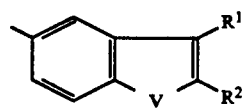
(FA)

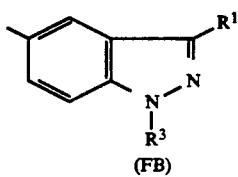
(FB)

wherein V, $R^1$, $R^2$ and $R^3$ are as defined above. Preferably, the group F represents an indole moiety of structure FC:

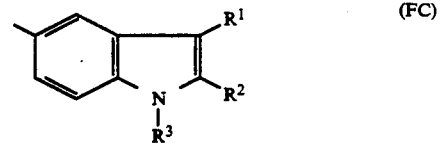

wherein $R^1$, $R^2$ and $R^3$ are as defined above, in particular wherein $R^2$ and $R^3$ are both hydrogen.

Suitable values for the group $A^1$ include hydrogen, and $C_{1-6}$ alkyl, $C_{3-7}$ cycloalkyl, aryl, aryl($C_{1-6}$)alkyl, $C_{3-7}$ heterocycloalkyl, heteroaryl or heteroaryl($C_{1-6}$)alkyl, any of which groups may be optionally substitued. Examples of optional substituents on the group $A^1$ suitably include trifluoromethyl, $C_{1-6}$ alkoxy, $C_{2-6}$ alkoxycarbonyl, $C_{2-6}$ alkylcarbonyl, $C_{1-6}$ alkylsulphonyl, arylsulphonyl, amino, mono- or di($C_{1-6}$)alkylamino, $C_{2-6}$ alkylcarbonylamino, arylcarbonylamino, $C_{2-6}$ alkoxycarbonylamino, $C_{1-6}$ alkylsulphonylamino, arylsulphonylamino, $C_{1-6}$ alkylsulphonylaminomethyl, aminocarbonylamino, mono- or di($C_{1-6}$)alkylaminocarbonylamino, mono- or diarylaminocarbonylamino, pyrrolidylcarbonylamino, aminocarbonyl, mono- or di($C_{1-6}$)alkylaminocarbonyl, $C_{1-6}$ alkylaminosulphonyl, aminosulphonylmethyl, and mono- or di($C_{1-6}$)alkylaminosulphonylmethyl.

Representative values of $A^1$ include hydrogen, methyl, ethyl, aminoethyl, acetylaminoethyl, benzoylaminoethyl, methoxycarbonylaminoethyl, ethoxycarbonylaminoethyl, t-butoxycarbonylaminoethyl, methylsulphonylaminoethyl, aminocarbonylaminoethyl, methylaminocarbonylaminoethyl, t-butylaminocarbonylaminoethyl, phenylaminocarbonylaminoethyl, pyrrolidylcarbonylaminoethyl, isopropyl, cyclopropyl, phenyl, methylsulphonylaminophenyl, aminocarbonylphenyl, methylaminocarbonylphenyl, methylsulphonylaminomethylphenyl, aminosulphonylmethylphenyl, methylaminosulphonylmethylphenyl, dimethylaminosulphonylmethylphenyl, benzyl, trifluoromethylbenzyl, methoxybenzyl, acetylaminobenzyl, methylsulphonylaminobenzyl, aminocarbonylaminobenzyl, aminocarbonylbenzyl, methylaminocarbonylbenzyl, methylsulphonylbenzyl, methylaminosulphonylbenzyl, pyridylmethyl and methoxypyridylmethyl. Particular values of $A^1$ include hydrogen, methyl, ethyl, isopropyl, benzyl and acetylaminobenzyl.

The groups $A^2$ and $A^3$ independently represent hydrogen or $C_{1-6}$ alkyl. The alkyl moiety is suitably a methyl or ethyl group, or a straight-chained or branched propyl, butyl, pentyl or hexyl group. Preferably, one of $A^2$ and $A^3$ represents hydrogen and the other represents hydrogen or $C_{1-6}$ alkyl, especially hydrogen or methyl. Where $A^2$ and $A^3$ are both other than hydrogen, it is preferred that these groups are identical. Moreover, where $A^2$ and $A^3$ are both other than hydrogen, it is particularly preferred that these groups are both attached to the same carbon atom, i.e. giving rise to gem-dialkyl substitution.

Representative values of $R^1$ include aminoethyl, N-methylaminoethyl, N,N-dimethylaminoethyl, 4-piperidyl, 1-methyl-4-piperidyl, 3-pyrrolidinyl and 1-methyl- 3-pyrrolidinyl. Preferably, $R^1$ represents aminoethyl, N-methylaminoethyl or N,N-dimethylaminoethyl.

Preferred values for the groups $R^2$ to $R^7$ are hydrogen and methyl.

A particular sub-class of compounds according to the invention is represented by the compounds of formula IIA, and salts and prodrugs thereof:

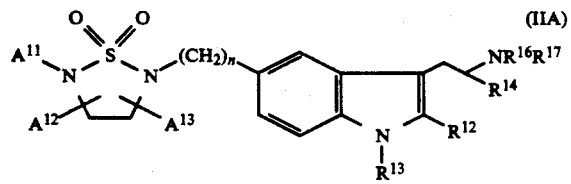

(IIA)

wherein n is zero, 1, 2 or 3, preferably zero, 1 or 2;

$A^{11}$ represents hydrogen; or $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl or heteroaryl($C_{1-6}$)alkyl, any of which groups may be optionally substituted; and $A^{12}$, $A^{13}$, $R^{12}$, $R^{13}$, $R^{14}$, $R^{16}$ and $R^{17}$ independently represent hydrogen or $C_{1-6}$ alkyl.

Examples of optional substituents on the group $A^{11}$ suitably include trifluoromethyl, $C_{1-6}$ alkoxy, $C_{2-6}$ alkoxycarbonyl, $C_{2-6}$ alkylcarbonyl, $C_{1-6}$ alkylsulphonyl, arylsulphonyl, amino, mono- or di($C_{1-6}$)alkylamino, $C_{2-6}$ alkylcarbonylamino, arylcarbonylamino, $C_{2-6}$ alkoxycarbonylamino, $C_{1-6}$ alkylsulphonylamino, arylsulphonylamino, $C_{1-6}$ alkylsulphonylaminomethyl, aminocarbonylamino, mono- or di($C_{1-6}$)alkylaminocarbonylamino, mono- or diarylaminocarbonylamino, pyrrolidylcarbonylamino, aminocarbonyl, mono- or di($C_{1-6}$)alkylaminocarbonyl, $C_{1-6}$ alkylaminosulphonyl, aminosulphonylmethyl, and mono- or di($C_{1-6}$)alkylaminosulphonylmethyl.

Particular values of $A^{11}$ with respect to formula IIA include hydrogen, methyl, ethyl, isopropyl, benzyl and acetylaminobenzyl.

Preferably one of $A^{12}$ and $A^{13}$ represents hydrogen and the other represents hydrogen or methyl, especially hydrogen. Alternatively, when $A^{12}$ and $A^{13}$ are both other than hydrogen, it is preferred that they are both methyl groups attached to the same carbon atom.

Preferably, $R^{12}$, $R^{13}$ and $R^{14}$ each represents hydrogen. Preferred values of $R^{16}$ and $R^{17}$ with respect to formula IIA include hydrogen and methyl.

Specific compounds within the scope of the present invention include:

3-[2-(dimethylamino)ethyl]-5-[(1,1-dioxo-5-methyl-1,2,5-thiadiazolidin-2-yl)methyl]-1H-indole;

3-(2-aminoethyl)-5-[(1,1-dioxo-5-methyl-1,2,5-thiadiazolidin-2-yl)methyl]-1H-indole;

3-[2-(dimethylamino)ethyl]-5-[2-(1,1-dioxo-5-methyl-1,2,5-thiadiazolidin-2-yl)ethyl]-1H-indole;

3-(2-aminoethyl)-5-[2-(1,1-dioxo-5-methyl-1,2,5-thiadiazolidin-2-yl)ethyl]-1H-indole;

3-[2-(dimethylamino)ethyl]-5-[(5-(4-acetylaminobenzyl)-1,1-dioxo-1,2,5-thiadiazolidin-2-yl)methyl]-1H-indole;

3-(2-aminoethyl)-5-[(5-(4-acetylaminobenzyl)-1,1-dioxo-1,2,5-thiadiazolidin-2-yl)methyl]-1H-indole;

3-(2-aminoethyl)-5-[(1,1-dioxo-1,2,5-thiadiazolidin-2-yl)methyl]-1H-indole;

3-(2-aminoethyl)-5-[(1,1-dioxo-5-isopropyl-1,2,5-thiadiazolidin-2-yl)methyl]-1H-indole;

3-(2-aminoethyl)-5-[2-(1,1-dioxo-1,2,5-thiadiazolidin-2-yl)ethyl]-1H-indole;

3-(2-aminoethyl)-5-[2-(1,1-dioxo-5-ethyl1,2,5-thiadiazolidin-2-yl)ethyl]-1H-indole;

3-[2-(dimethylamino)ethyl]-5-[(1,1-dioxo-1,2,5-thiadiazolidin-2-yl)methyl]-1H-indole;

3-[2-(dimethylamino)ethyl]-5-[(1,1-dioxo-5-isopropyl-1,2,5-thiadiazolidin-2-yl)methyl]-1H-indole;

3-[2-(dimethylamino)ethyl]-5-[2-(1,1-dioxo-1,2,5-thiadiazolidin-2-yl)ethyl]-1H-indole;

3-[2-(dimethylamino)ethyl]-5-[2-(1,1-dioxo-5-ethyl-1,2,5-thiadiazolidin-2-yl)ethyl]-1H-indole;

3-[2-(methylamino)ethyl]-5-[(1,1-dioxo-5-methyl-1,2,5-thiadiazolidin-2-yl)methyl]-1H-indole;

3-(2-aminoethyl)-5-[(1,1-dioxo-6-methyl-3,4,5,6-tetrahydro-1,2,6-thiadiazin-2-yl)methyl]-1H-indole;

3-[2-(dimethylamino)ethyl]-5-[(1,1-dioxo-6-methyl-3,4,5,6-tetrahydro-1,2,6-thiadiazin-2-yl)methyl]-1H-indole;

3-(2-aminoethyl)-5-[(4,4-dimethyl-1,1-dioxo-1,2,5-thiadiazolidin-2-yl)methyl]-1H-indole;

3-(2-aminoethyl)-5-[(3,3-dimethyl-1,1-dioxo-1,2,5-thiadiazolidin-2-yl)methyl]-1H-indole;

3-(2-aminoethyl)-5-(1,1-dioxo-5-methyl-1,2,5-thiadiazolidin-2-yl)-1H-indole;

3-(2-aminoethyl)-5-(5-benzyl-1,1-dioxo-1,2,5-thiadiazolidin-2-yl)-1H-indole;

3-[2-(dimethylamino)ethyl]-5-[(4,4-dimethyl-1,1-dioxo-1,2,5-thiadiazolidin-2-yl)methyl]-1H-indole;

3-[2-(dimethylamino)ethyl]-5-[(3,3-dimethyl-1,1-dioxo-1,2,5-thiadiazolidin-2-yl)methyl]-1H-indole;

3-[2-(dimethylamino)ethyl]-5-(1,1-dioxo-5-methyl-1,2,5-thiadiazolidin-2-yl)-1H-indole;

3-[2-(dimethylamino)ethyl]-5-(5-benzyl-1,1-dioxo-1,2,5-thiadiazolidin-2-yl)-1H-indole;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a nontoxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to this invention may be prepared by a process which comprises reacting a compound of formula W—E—F with a compound of formula III:

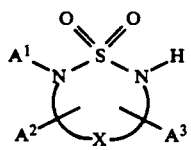

(III)

wherein X, $A^1$, $A^2$, $A^3$, E and F are as defined above, and W represents a group which is capable of being displaced during the course of the reaction.

The displaceable group W suitably represents hydroxy, in which case the reaction is advantageously carried out in the presence of triphenylphosphine and diethyl azodicarboxylate, ideally in an organic solvent such as tetrahydrofuran at room temperature.

Alternatively, the group W may be a conventional leaving group such as a halogen atom, for example bromine, or a trialkylammonium group, for example trimethylammonium. Where W represents bromine, the reaction is conveniently carried out in the presence of a mild base, e.g. potassium carbonate, suitably in an organic solvent such as N,N-dimethylformamide, at a temperature of between 10° C. and 100° C., ideally at room temperature. Where W represents trimethylammonium, the reaction is conveniently carried out in the presence of a strong base such as sodium hydride, suitably in an organic solvent such as N,N-dimethylformamide, and ideally at a temperature in the region of 90° C.

Where they are not commercially available, the intermediates of formula W—E—F may be prepared by procedures analogous to those described in the accompanying Examples, or by methods well known from the art. For example, those compounds wherein W is halogen and E is other than a bond may be prepared from the corresponding compounds of formula W—E—F in which W is hydroxy using standard halogenation techniques. Alternatively, those compounds wherein W is a trialkylammonium group may be prepared from the corresponding compounds of formula W—E—F in which W represents dialkylamino by quaternisation using a suitable alkyl iodide in conventional manner.

Where the group F is an indole moiety of structure FC as defined above, the compound of formula W—E—F may be prepared by reacting a compound of formula IV:

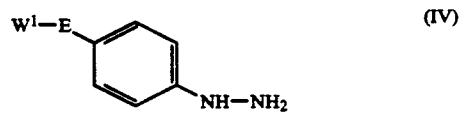

(IV)

wherein $W^1$ corresponds to the group W as defined above, or represents a protected derivative thereof or a precursor thereto; and E is as defined above; with a compound of formula V or a carbonyl-protected form thereof:

(V)

wherein $R^2$ is as defined above and $R^{11}$ corresponds to the group $R^1$ as defined above or represents a group of formula $-CH_2.CHR^4D^1$, in which $R^4$ is as defined above and $D^1$ represents a readily displaceable group; followed, where required, by (i) N-alkylation by standard methods to introduce the moiety $R^3$, and (ii) deprotection or interconversion of the moiety $W^1$ to the desired group W.

Where the moiety $W^1$ in the compounds of formula IV represents a precursor to a hydroxy group, this is suitably a $C_{1-4}$ alkyl ester group, e.g. methoxycarbonyl or ethoxycarbonyl, which can subsequently be converted to the required hydroxy group by reduction using, for example, diisobutylaluminium hydride (DIBAL-H) in tetrahydrofuran at −30° C.

Alternatively, where $W^1$ represents the precursor to a trialkylammonium group, this is suitably a cyano moiety, which can subsequently be reduced by catalytic hydrogenation; the resulting aminomethyl group can in turn be alkylated, and finally quaternised using a suitable alkyl iodide, to afford the desired trialkylammonium group.

Suitable carbonyl-protected forms of the compounds of formula V include the dimethyl acetal or ketal derivatives.

The readily displaceable group $D^1$ in the compounds of formula V suitably represents a halogen group, preferably chlorine. When the moiety $R^{11}$ in the compounds of formula V is a group of formula $-CH_2.CHR^4D^1$, the substituent $D^1$ is displaced in situ under the prevailing reaction conditions to afford a final product of formula I wherein $R^1$ represents a group of formula $-CH_2.CHR^4.NH_2$. The terminal amino group can subsequently, if desired, be further elaborated using techniques known from the art to give a compound of formula I wherein $R^1$ represents the required group of formula $-CH_2.CHR^4.NR^6R^7$.

The reaction of compounds IV and V may be carried out in a single step (Fiscer indole synthesis) or by an initial non-cyclising step at a lower temperature to give a compound of formula VI:

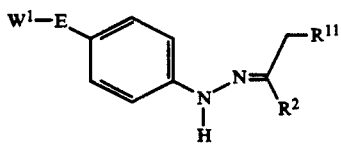 (VI)

wherein $W^1$, E, $R^2$ and $R^{11}$ are as defined above; followed by cyclisation using a suitable reagent, such as a polyphosphate ester.

The hydrazines of formula IV may be prepared from the corresponding anilines of formula VII:

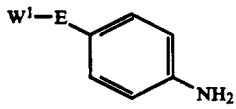 (VII)

wherein $W^1$ and E are as defined above; by diazotisation followed by reduction. Diazotisation is typically carried out using sodium nitrite/conc. HCl and the resulting diazo product reduced in situ using, for example, tin(II) chloride/conc. HCl.

The anilines of formula VII may be prepared by reduction of the corresponding nitro compounds of formula VIII:

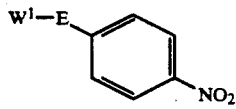 (VIII)

wherein $W^1$ and E are as defined above; typically by catalytic hydrogenation or using tin(II) chloride.

Where they are not commercially available, the nitro compounds of formula VIII may be synthesized by standard methods well known to those skilled in the art.

Where the group F is an indazole moiety of structure FB as defined above, the compound of formula W—E—F may be prepared by the cyclisation of a compound of formula IX:

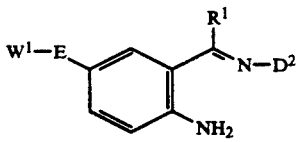 (IX)

wherein $W^1$, E and $R^1$ are as defined above; and $D^2$ represents a readily displaceable group; followed, where required, by (i) N-alkylation by standard methods to introduce the moiety $R^3$, and (ii) deprotection or interconversion of the moiety $W^1$ to the desired group W.

The cyclisation of compound IX is conveniently achieved in a suitable organic solvent at an elevated temperature, for example in a mixture of m-xylene and 2,6-lutidine at a temperature in the region of 140° C.

The readily displaceable group $D^2$ in the compounds of formula IX suitably represents a $C_{1-4}$ alkanoyloxy group, preferably acetoxy. Where $D^2$ in the desired compound of formula IX represents acetoxy, this compound may be conveniently prepared by treating a carbonyl compound of formula X:

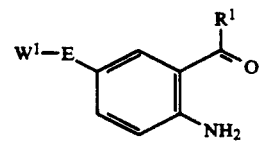 (X)

wherein $R^1$, E and $W^1$ are as defined above; or a protected derivative thereof; with hydroxylamine hydrochloride, advantgeously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivative of the intermediate of formula X may be conveniently prepared by ozonolysis of an indole derivative of formula XI:

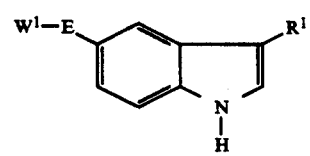 (XI)

wherein $R^1$, E and $W^1$ are as defined above; followed by a reductive work-up, advantageously using dimethyl sulphide.

The indole derivative of formula XI may be prepared by methods analogous to those described in the accompanying Examples, or by procedures well known from the art.

In an alternative process, the compounds according to the invention wherein the group F is an indole moiety of formula FC as defined above may be prepared by a method which comprises reacting a compound of formula XII:

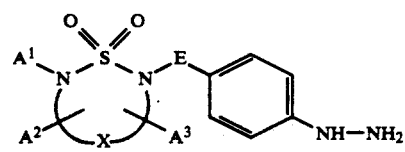 (XII)

wherein X, $A^1$, $A^2$, $A^3$ and E are as defined above; with a compound of formula V as defined above, or a carbonyl-protected form thereof, e.g. the dimethyl acetal or ketal; followed, where required, by N-alkylation by standard methods to introduce the moiety $R^3$.

As with that between compounds IV and V, the reaction between compounds XII and V may be carried out in a single step (Fischer indole synthesis) or by an initial non-cyclising step at a lower temperature to give a compound of formula XIII:

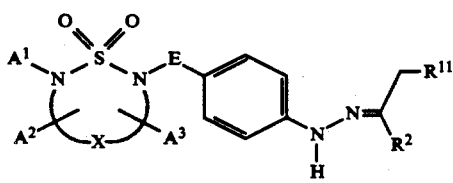 (XIII)

wherein X, $A^1$, $A^2$, $A^3$, E, $R^2$ and $R^{11}$ are as defined above; followed by cyclisation using a suitable reagent, e.g. a polyphosphate ester.

The hydrazines of formula XII may be prepared from the corresponding anilines of formula XIV:

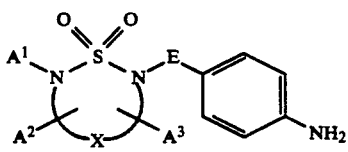
(XIV)

wherein X, $A^1$, $A^2$, $A^3$ and E are as defined above; by methods analogous to those described above with reference to the compounds of formula VII.

The anilines of formula XIV may be prepared by reduction of the corresponding nitro compounds of formula XV:

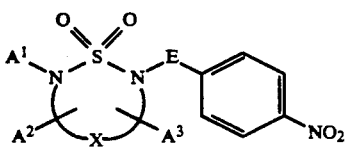
(XV)

wherein X, $A^1$, $A^2$, $A^3$ and E are as defined above; typically by catalytic hydrogenation or using tin (II) chloride.

The intermediates of formula XV may be prepared by reaction of a compound of formula III as defined above with a compound of formula XVI:

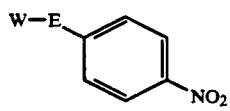
(XVI)

wherein W and E are as defined above; under reaction conditions analogous to those described above for the reaction between the compound of formula W-E-F and the compound of formula III.

When the moiety W in the compounds of formula XVI is attached directly to the aromatic ring, i.e. when E represents a bond, it is preferred that W represents fluorine. In this case, the reaction is conveniently carried out in the presence of sodium hydride using N,N-dimethylformamide as solvent, ideally at the reflux temperature of the solvent.

Where they are not commercially available, the nitro compounds of formula XVI may be synthesized by standard methods well known to those skilled in the art.

In a further process, the compounds according to the invention wherein the group F is an indazole moiety of formula FB as defined above may be prepared by a method which comprises cyclising a compound of formula XVII:

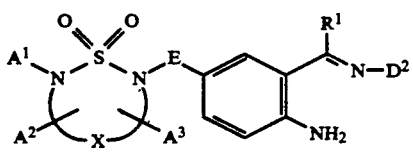
(XVII)

wherein X, $A^1$, $A^2$, $A^3$, E, $R^1$ and $D^2$ are as defined above; followed, where required, by N-alkylation by standard methods to introduce the moiety $R^3$.

As with the cyclisation of compound IX, that of compound XVII is conveniently achieved in a suitable organic solvent at an elevated temperature, for example in a mixture of m-xylene and 2,6-lutidine at a temperature in the region of 140° C.

The compounds of formula XVII may, for example, be prepared from the corresponding compound of formula XVIII:

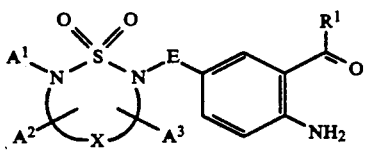
(XVIII)

wherein X, $A^1$, $A^2$, $A^3$, E and $R^1$ are as defined above; or a protected derivative thereof; which in turn may be prepared from the corresponding compound of formula XIX:

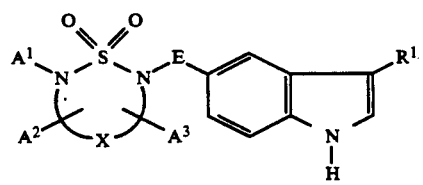
(XIX)

wherein X, $A^1$, $A^2$, $A^3$, E and $R^1$ are as defined above; using methods analogous to those described above with reference to the compounds of formulae X and XI. Thus, for example, since $W^1$ in the compounds of formula XI represents or is convertible into a group W, the compounds of formula XIX may be prepared therefrom by reaction with a compound of formula III.

The intermediates of formula III may be prepared by a method based on those described in *Indian J. Chem.*, 1982, 21B, 941, and *Chem. Ber.*, 1978, 111, 1915. In essence, this comprises reacting a compound of formula XX with a compound of formula XXI:

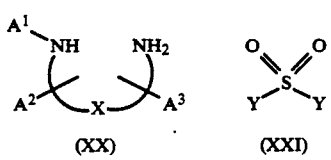

(XX)    (XXI)

wherein X, $A^1$, $A^2$ and $A^3$ are as defined above; and Y represents halogen, e.g. chlorine, or amino.

Where Y represents halogen, the reaction is conveniently carried out in chloroform at −50° C. Alternatively, where Y represents amino, the reaction is conveniently carried out in pyridine at reflux.

In a variant of this method, a compound of formula III wherein $A^1$ is t-butyl may be converted into a desired compound of formula III wherein $A^1$ is other than t-butyl by means of the following sequence:

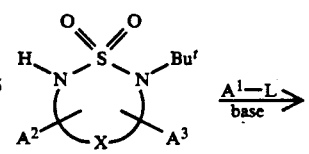

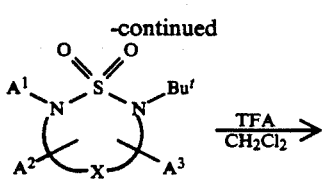

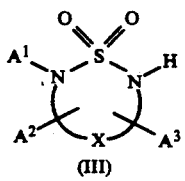

wherein $A^1$, $A^2$, $A^3$ and X are as defined above; L represents a leaving group such as halogen, e.g. chlorine; and TFA is an abbreviation for trifluoroacetic acid. A suitable base for use in the first step of the sequence is potassium carbonate.

It will be understood that any compound of formula I initially obtained from any of the above processes may, where appropriate, subsequently be elaborated into a further compound of formula I by techniques known from the art. For example, a compound of formula I wherein $R^3$ is hydrogen initially obtained may be converted into a compound of formula I wherein $R^3$ represents $C_{1-6}$ alkyl, $C_{2-6}$ alkenyl or $C_{2-6}$ alkynyl by standard techniques such as alkylation, for example by treatment with an alkyl iodide, e.g. methyl iodide, typically under basic conditions, e.g. sodium hydride in dimethylformamide, or triethylamine in acetonitrile. Similarly, a compound of formula I wherein $R^1$ represents a group of formula —$CH_2.CHR^4.NH_2$ initially obtained may be converted into a compound of formula I wherein $R^1$ represents a group of formula —$CH_2.CHR^4.NR^6R^7$ in which $R^6$ and $R^7$ are as defined above with the exception of hydrogen, for example by conventional N-alkylation or N-arylation techniques, e.g. by treatment with the appropriate aldehyde in the presence of a reducing agent such as sodium cyanoborohydride. Alternatively, a compound of formula I wherein $R^1$ represents a group of formula —$CH_2.CHR^4.NHMe$ can be prepared from the corresponding N-formyl derivative by reduction with borane-tetrahydrofuran complex.

Where the above-described processes for the preparation of the compounds according to the invention give rise to mixtures of stereoisomers, these isomers may be separated by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (—)-di-p-toluoyl-d-tartaric acid and/or (+)-di-p-toluoyl-l-tartaric acid followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene, *Protective Groups in Organic Synthesis*, John Wiley & Sons, 1981. The protecting groups may be removed at a convenient subsequent stage using methods known from the art.

The following Examples illustrate the preparation of compounds according to the invention.

The ability of test compounds to bind to 5-HT$_1$-like receptors was measured in membranes prepared from pig caudate using the procedure described in *J. Neurosci.*, 1987, 7, 894. Binding was determined using 2 nM 5-hydroxytryptamine creatinine sulphate, 5-[1,2-$^3$H(N)] as a radioligand. Cyanopindolol (100 nM) and mesulergine (100 nM) were included in the assay to block out 5-HT$_{1A}$ and 5-HT$_{1C}$ binding sites respectively. The concentration of the compounds of the accompanying Examples required to displace 50% of the specific binding (IC$_{50}$) is below 1 μM in each case.

The activity of test compounds as agonists of the 5-HT$_1$-like receptor was measured in terms of their ability to mediate contraction of the saphenous vein of New Zealand White rabbits, using the procedure described in *Arch. Pharm.*, 1990, 342, 111. Agonist potencies were calculated as -log$_{10}$EC$_{50}$(pEC$_{50}$) values, from plots of percentage 5-HT (1 μm) response against the concentration of the agonist. The compounds of the accompanying Examples were found to possess pEC$_{50}$ values in this assay of not less than 5.0 in each case.

INTERMEDIATE I

3-[2-(N-Tert-butyloxycarbonylamino)ethyl]-5-hydroxymethyl-1H-indole

1. 4-Carbethoxyphenylhydrazine Hydrochloride

To a cooled (—13° C.) and stirred suspension of ethyl 4-aminobenzoate (100 g, 605.3 mmol) in concentrated hydrochloric acid (780 ml) was added dropwise a solution of sodium nitrite (43.9 g, 635.9 mmol) in water (312 ml) at such a rate as to keep the temperature below —4° C. (ca 50 minutes). After being stirred for further 10 minutes at —5° C., the mixture was quickly filtered to remove solids and the clear yellow filtrate was added portionwise to a cooled (—20° C.) and stirred solution of tin (II) chloride dihydrate (682.9 g, 3.02 mmol) in concentrated hydrochloric acid (470 ml) at such a rate as to maintain the temperature below —10° C. (ca 25 minutes). The resulting mixture was allowed to warm to —5° C. over 25 min and the solid was collected by filtration, washed with diethyl ether (2×300 ml) and dried over phosphorous pentoxide-potassium hydroxide at 60° C. in vacuum oven to give 131.8 g (100%) of the title compound as a white solid. A sample recrystallized from absolute ethanol showed: mp 208°-212° C. (needles); δ$_H$ (360 MHz, DMSO-d$_6$) 10.42 (3H, br s, —N$^+$H$_3$), 8.92 (1H, br s, —NH—), 7.86 (2H, d, J=8.8 Hz, Ar-H), 7.01 (2H, d, J=8.8 Hz, Ar-H), 4.26 (2H, q, J=7.1 Hz, —OCH$_2$—), 1.30 (3H, t, J=7.1 Hz, —CH$_3$); m/z (CI) 181 (M$^+$+1).

2. Ethyl 3-(2-aminoethyl)-1H-indole-5-carboxylate. Hydrochloride

A solution of 4-carbethoxyphenylhydrazine hydrochloride (130 g, 598 mmol) and 4-chlorobutanal dimethylacetal (86.6 g, 568 mmol) in ethanol-water (5:1, 4 L) was stirred at room temperature for 20 minutes and then it was heated at reflux for 4.5 hours. Solvents were removed under vacuum, the remaining residue was dissolved in hot ethanol (1 L) and products were precipitated by addition of diethyl ether (1.5 L). The solid was filtered off and recrystallised from a mixture of hot ethanol (200 ml) and acetone (1 L) to give 55.4 g (34.5%) of the title compound as a pale yellow solid; $\delta_H$ (360 MHz, DMSO-d$_6$) 11.43 (1H, s, indole N—H), 8.26 (1H, s, Ar—H), 8.03 (3H, br s, —N$^+$H$_3$), 7.73 (1H, dd, J=8.6 and 1.6 Hz, Ar—H), 7.45 (1H, d, J=8.6 Hz, Ar—H), 7.38 (1H, d, J=2.2 Hz, Ar—H), 4.32 (2H, q, J=7.1 Hz, —OCH$_2$—), 3.06 (4H, s, —CH$_2$CH$_2$—), 1.34 (3H, t, J=7.1 Hz, —CH$_3$); m/z (CI) 231 (M$^+$-1).

3. Ethyl 3-[2-(N-tert-butyloxycarbonylamino)ethyl]-1H-indole-5-carboxylate

To a cooled (−10° C.) and stirred suspension of ethyl 3-(2-aminoethyl)-1H-indole-5-carboxylate hydrochloride (26.9 g, 100 mmol) in anhydrous dichloromethane (900 ml) was added anhydrous triethylamine (28.7 ml, 200 mmol) followed by di-tert-butyldicarbonate (24.0 g, 110 mmol) and the resulting mixture was stirred at that temperature for 30 minutes and at room temperature for 3 hours, under nitrogen. The reaction mixture was diluted with dichloromethane (300 ml), washed with 2N hydrochloric acid (2×100 ml), 10% aqueous sodium bicarbonate (100 ml), brine (100 ml), dried (MgSO$_4$) and concentrated. Flash chromatography (silica gel, dichloromethane-methanol, 96:4) of the residue followed by crystallisation of the product from absolute ethanol gave 23.3 g (70%) of the required title compound as white crystals; mp 170°-171° C.; $\delta_H$ (360 MHz, CDCl$_3$) 8.35 (1H, s, Ar—H), 8.28 (1H, br s, indole N—H), 7.91 (1H, dd, J=8.5 and 1.6 Hz, Ar—H), 7.36 (1H, d, J=8.5 Hz, Ar—H), 7.09 (1H, br s, Ar—H), 4.61 (1H, br s, —NH—), 4.40 (2H, q, J=7.2 Hz, —OCH$_2$—), 3.48 (2H, m, —CH$_2$N—), 2.16 (2H, t, J=6.3 Hz, —CH$_2$—), 1.43 (9H, s, t-Bu), 1.42 (3H, t, J=7.2 Hz, —CH$_3$); m/z (EI) 332 (M$^+$). (Found: C, 65.27; H, 7.59; N, 8.40. C$_{18}$H$_{24}$N$_2$O$_4$ requires: C, 65.04; H, 7.28; N, 8.43%).

4. 3-[2-(N-Tert-butyloxycarbonylamino)ethyl]-5-hydroxymethyl-1H-indole

To a cooled (−50° C.) and stirred solution of the product from Step 3 (17.4 g, 52.4 mmol) in anhydrous tetrahydrofuran (650 ml) was added dropwise via cannula diisobutylaluminium hydride (1M in toluene; 168 ml) over 23 minutes, under a nitrogen atmosphere. After being stirred at −25° C. for 1 hour, additional diisobutylaluminium hydride (1M in toluene; 40 ml) was added dropwise over 15 minutes and stirring was continued at −25° C. for further 30 minutes. Methanol (65 ml) was added dropwise (CAUTION! H$_2$ evolution) at −35° C. followed by aqueous citric acid (10%; 450 ml) and the organic phase was decanted off. The aqueous solution was extracted with ethyl acetate (500 ml) and the combined organic phases were washed with brine (1×200 ml), dried (Na$_2$SO$_4$) and concentrated. Flash chromatography (silica gel, dichloromethane-methanol, 97:3) of the remaining residue gave 13.8 g (90.8%) of the title compound as a white solid. A sample recrystallised from dichloromethane showed: mp 129°-130° C.; $\delta_H$(360 MHz, DMSO-d$_6$) 10.70 (1H, br s, indole N—H), 7.44 (1H, s, Ar—H), 7.26 (1H, d, J=8.3 Hz, Ar—H), 7.10 (1H, s, Ar—H), 7.03 (1H, d, J=8.3 Hz, Ar—H), 6.86 (1H, br t, —NH—), 4.95 (1H, t, J=5.6 Hz, —OH), 4.54 (2H, d, J=5.6 Hz, —CH$_2$OH), 3.18 (2H, m, —CH$_2$N—), 2.78 (2H, t, J=7.2 Hz, —CH$_2$—), 1.38 (9H, s, t-Bu); m/z (EI) 290 (M$^+$). (Found: C, 65.95; H, 7.82; N, 9.37. C$_{16}$H$_{22}$N$_2$O$_3$ requires: C, 66.18; H, 7.64; N, 9.65%).

INTERMEDIATE 2

3-[2(N-Tert-butyloxycarbonylamino)ethyl]-5-(2-hydroxyethyl)-1H-indole

1. 4-(Carbethoxymethyl)phenylhydrazine Hydrochloride

The title compound was prepared from ethyl 4-aminophenylacetate by a similar method to that described for Intermediate 1 (Step 1); mp 171°-174° C. (absolute ethanol); $\delta_H$(360 MHz, DMSO-d$_6$) 10.02 (br s, —N$^+$H$_3$), 8.14 (br s, —NH—), 7.16 (2H, d, J=8.5 Hz, Ar—H), 6.92 (2H, d, J=8.5 Hz, Ar—H), 4.06 (2H, q, J=7.1 Hz, —OCH$_2$—), 3.56 (2H, s, Ar—CH$_2$—), 1.17 (3H, t, J=7.1 Hz, —CH$_3$); m/z (EI) 194 (M$^+$).

2. Ethyl 3-(2-aminoethyl)-1H-indole-5-acetate. Hydrochloride

The title compound was prepared from 4-(carbethoxymethyl)phenylhydrazine hydrochloride and 4-chlorobutanal dimethylacetal by a similar method to that described for Intermediate 1 (Step 2); mp 204°-206° C. (ethanol-diethyl ether); $\delta_H$ (360 MHz, DMSO-d$_6$) 10.70 (1H, br s, indole N—H), 8.09 (3H, br s, —N$^+$H$_3$), 7.43 (1H, s, Ar—H), 7.31 (1H, d, J=8.3 Hz, Ar—H), 7.23 (1H, d, J=2.3 Hz, Ar—H), 6.99 (1H, dd, J=8.3 and 1.6 Hz, Ar—H), 4.07 (2H, q, J=7.1 Hz, —OCH$_2$—), 3.68 (2H, s, Ar—CH$_2$CO—), 3.02 (4H, m, —CH$_2$CH$_2$—), 1.18 (3H, t, J=7.1 Hz, —CH$_3$); m/z (CI) 247 (M$^+$+1).

3. Ethyl 3-[2-(N-tert-butyloxycarbonylamino)ethyl]-1H-indole-5-acetate

The title compound was prepared in 98% yield from ethyl 3-(2-aminoethyl)-1H-indole-5-acetate by a similar method to that described for Intermediate 1 (Step 3); colourless thick oil; $\delta_H$(360 MHz, CDCl$_3$), 8.06 (1H, br s, indole N—H), 7.48 (1H, s, Ar—H), 7.30 (1H, d, J=8.3 Hz, Ar—H), 7.13 (1H, d, J=8.3 Hz, Ar—H), 6.99 (1H, s, Ar—H), 4.58 (1H, br s, —NH—), 4.15 (2H, q, J=7.1 Hz, —OCH$_2$—), 3.70 (2H, s, Ar—CH$_2$—CO—), 3.45 (2H, m, —CH$_2$N—), 2.92 (2H, t, J=6.8 Hz, —CH$_2$—), 1.43 (9H, s, t—Bu), 1.25 (3H, t, J=7.1 Hz, —CH$_3$); m/z (EI) 346 (M$^+$).

4. 3-[2-(N-Tert-butyloxycarbonylamino)ethyl]-5-(2-hydroxyethyl)-1H-indole

Diisobutylaluminium hydride reduction of ethyl 3-[2-(N-tert-butyloxycarbonylamino)ethyl]-1H-indole-5-acetate using the conditions described for Intermediate 1 (Step 4) afforded the title compound as a colourless thick oil, after purification by flash chromatography (silica gel, diethyl ether); $\delta_H$ (250 MHz, CDCl$_3$) 8.03 (1H, br s, indole N—H), 7.44 (1H, s, Ar—H), 7.32 (1H, d, J=8.3 Hz, Ar—H), 7.07 (1H, dd, J=8.3 and 1.6 Hz, Ar—H), 7.02 (1H, d, J=2.2 Hz, Ar—H), 4.60 (1H, br s, —NH—), 3.89 (2H, t, J=6.5 Hz, —CH$_2$OH), 3.45 (2H, m, —CH$_2$N—), 2.97 (2H, t, J=6.5 Hz, —CH$_2$C-H$_2$OH), 2.93 (2H, t, J=6.8 Hz, —CH$_2$—), 1.43 (9H, s, t—Bu); m/z (CI) 303 (M$^+$-1). (Found: m/z 304.1759. C$_{17}$H$_{24}$N$_2$O requires: m/z 304.1787).

INTERMEDIATE 3

3-[2-(N-Tert-butyloxycarbonylamino)ethyl]-5-trimethylammoniummethyl-1H-indole Iodide

1. 4-Cyanophenylhydrazine. Hydrochloride

To a cooled (−15° C.) and stirred suspension of 4-aminobenzonitrile (50 g, 423 mmol) in concentrated hydrochloric acid (550 ml) was added dropwise a solution of sodium nitrite (31.5 g, 457 mmol) in water (200 ml) at such a rate as to maintain the temperature below −10° C. After the addition was finished, the reaction mixture was quickly filtered to remove solids and the filtrate was added portionwise to a cooled (−20° C.) and stirred solution of tin (II) chloride dihydrate (477 g, 2.1 mol) in concentrated hydrochloric acid (370 ml) at such a rate as to maintain the temperature below −10° C. After further 15 minutes at −10° to 0° C., the white precipitate was collected by filtration, washed with diethyl ether (4×250 ml) and dried to give 56 g (78%) of the title compound; mp 235°-237° C. (ethanol-water 1:1); $\delta_H$ (250 MHz, DMSO-$d_6$) 10.50 (3H, br s, —$N^+H_3$), 9.10 (1H, br s, —NH—), 7.71 (2H, d, J=8.8 Hz, Ar—H), 7.03 (2H, d, J=8.8 Hz, Ar—H); m/z (CI) 132 (M+-1).

2. 3-(2-Aminoethyl)-5-cyano-1H-indole. Hydrochloride

To a stirred suspension of 4-cyanophenylhydrazine (50 g) in a mixture of ethanol and water (5:1; 2l) was added 4-chlorobutanal dimethylacetal (45 g) and the resulting mixture was refluxed for 18 hours. Solvents were removed under vacuum and the residue was azeotroped with toluene to give a brown solid. Crystallisation of this crude material from methanol (150 ml) gave 23 g (35%) of the title compound as a yellow solid; mp 270°-274° C.; $\delta_H$ (250 MHz, DMSO-$d_6$) 11.60 (1H, br s, indole N—H), 8.17 (1H, d, J=1.1 Hz, Ar—H), 7.97 (3H, br s, —$N^+H_3$), 7.54 (1H, d, J=8.5 Hz, Ar—H), 7.46 (1H, s, Ar—H), 7.44 (1H, dd, J=8.5 and 1.1 Hz, Ar—H), 3.05 (4H, br s, —$CH_2CH_2N$—); m/z (CI) 184 (M+-1).

3. 3-[2-(N-Tert-butyloxycarbonylamino)ethyl]-5-cyano-1H-indole

The title compound was prepared in 58% yield from 3-(2-aminoethyl)-5-cyano-1H-indole hydrochloride using the conditions described for Intermediate 1 (Step 3); white solid; mp 132°-134° C. (hexane-ethyl acetate); $\delta_H$(250 MHz, CDCl$_3$) 8.42 (1H, br s, indole N—H), 7.93 (1H, s, Ar—H), 7.41 (2H, s, Ar—H), 7.12 (1H, d, J=2.2 Hz, Ar—H), 4.71 (1H, br s, —NH—), 3.44 (2H, q, J=6.9 Hz, —$CH_2NH$—), 2.94 (2H, t, J=6.9 Hz, Ar—$CH_2$—), 1.45 (9H, s, t-Bu); m/z (CI) 286 (M++1).

4. 5-Aminomethyl-3-[2-(N-tert-butyloxycarbonylamino)ethyl]-1H-indole

A solution of the product from the previous step (11.3 g) in a mixture of absolute ethanol (750 ml) and chloroform (22 ml) was hydrogenated at 50 psi over platinum (IV) oxide (1 g) for 28 hours. The catalyst was removed by filtration and solvents were removed under vacuum. Flash chromatography of the residue (silica gel, dichloromethane-methanol-ammonia 90:10:1) gave 9.5 g (82%) of the title compound as a ehite solid; mp 147°-149° C.; $\delta_H$ (360 MHz, CDCl$_3$) 8.04 (1H, br s, indole N—H), 7.52 (1H, s, Ar—H), 7.33 (1H, d, J=8.4 Hz, Ar—H), 7.16 (1H, d, J=8.4 Hz, Ar—H), 7.03 (1H, s, Ar—H), 4.61 (1H, br s, —NHBOC), 3.96 (2H, s, Ar—$CH_2NH_2$), 3.45 (2H, br q, —$CH_2NHBOC$), 2.95 (2H, t, J=6.8 Hz, Ar-$CH_2$—), 1.43 (9H, s, t-Bu); m/z (CI) 288 (M+-1).

5. 3-[2-(N-Tert-butyloxycarbonylamino)ethyl]-5-dimethylaminomethyl-1H-indole The title compound was prepared in 71% yield from 5-aminomethyl-3-[2-(N-tert-butyloxycarbonylamino)ethyl]-1H-indole using the conditions described for Example 2; colourless thick oil; $\delta_H$(250 MHz, CDCl$_3$) 8.07 (1H, br s, indole N—H), 7.50 (1H, s, Ar—H), 7.31 (1H, d, J=8.3 Hz, Ar—H), 7.16 (1H, d, J=8.3 Hz, Ar—H), 7.02 (1H, s, Ar—H), 4.61 (1H, br s, —NH—), 3.54 (2H, s, Ar—$CH_2N$—), 3.45 (2H, q, J=6.2 Hz, —$CH_2NH$—), 2.94 (2H, t, J=6.2 Hz, Ar—$CH_2$—), 2.27 (6H, s, —N$Me_2$), 1.43 (9H, s, t-Bu).

6. 3-[2-(N-Tert-butyloxycarbonylamino)ethyl]-5-trimethylammoniummethyl-1H-indole iodide A solution of the product from step 5 (2.9 g) in a mixture of anhydrous diethyl ether (170 ml) and iodomethane (36 ml) was allowed to stand at room temperature for 16 hours in the dark. The white solid was collected by filtration, washed with diethyl ether and dried over phosphorous pentoxide at 50° C. under vacuum to give 4.2 g (100%) of the title compound; mp 199°-202° C. (decomposition); $\delta_H$ (360 MHz, DMSO-$d_6$) 11.09 (1H, br s, indole N—H), 7.69 (1H, s, Ar—H), 7.44 (1H, d, J=8.3 Hz, Ar—H), 7.26 (1H, s, Ar—H), 7.19 (1H, d, J=8.3 Hz, Ar—H), 6.89 (1H, br t, —NH—), 4.57 (2H, s, Ar—$CH_2N$—), 3.23 (2H, q, J=7.6 Hz, —$CH_2NH$—), 3.01 (9H, s, —$N^+Me_3$), 2.83 (2H, t, J=7.6 Hz, Ar—$CH_2$—), 1.37 (9H, s, t-Bu); m/z (FAB) 332. (Found: C, 49.30; H, 6.55; N, 8.79. $C_{19}H_{30}IN_3O_2$ requires: C, 49.68; H, 6.58; N, 9.15%).

EXAMPLE 1

3-(2-Aminoethyl)-5-[(1,1-dioxo-5-methyl-1,2,5-thiadiazolidin-2-yl)methyl]-1H-indole

Method A

1. 3-[2-(N-Tert-butyloxycarbonylamino)ethyl]-5-[(1,1-dioxo-5-methyl-1,2,5-thiadiazolidin-2-yl)methyl]-1H-indole To a solution of Intermediate I (615 mg, 2.19 mmol), triphenylphosphine (666 mg, 2.54 mmol) and 2-methyl-1,2,5-thiadiazolidine-1,1-dioxide (346 mg, 2.54 mmol) [V. P. Arya, K. Nagarajan, S. J. Shenoy, *Indian J. Chem.*, 1982, 21B, 941] in anhydrous tetrahydrofuran (12 ml) was added dropwise, under nitrogen, diethyl azodicarboxylate (400 μl, 2.54 mmol) over 18 minutes. After being stirred at room temperature for 3 hours, solvents were removed under vacuum and the remaining residue was purified by flash chromatography (silica gel, dichloromethane-methanol, 98:2; and hexane-ethyl acetate, 40:60) to give 460 mg (51.5%) of the title compound as a colourless thick oil; $\delta_H$ (360 MHz, CDCl$_3$) 8.09 (1H, br s, indole N—H), 7.54 (1H, s, Ar—H), 7.35 (1H, d, J=8.4 Hz, Ar—H), 7.22 (1H, dd, J=8.4 and 1.5 Hz, Ar—H), 7.06 (1H, s, Ar—H), 4.60 (1H, br s, —NH—), 4.30 (2H, s, Ar—$CH_2N$—), 3.44 (2H, m, —$CH_2NH$—), 3.25 (2H, dd, J=8.2 and 7.0 Hz, —$CH_2$—), 3.15 (2H, dd, J=8.2 and 7.0 Hz, —$CH_2$—), 2.94 (2H, t, J=6.8 Hz, Ar—CH$_2$CH$_2$N—) 2.79 (3H, s, —NMe), 1.43 (9H, s, t-Bu); m/z (EI) 408 (M+).

2.
3-(2-Aminoethyl)-5-[(1,1-dioxo-5-methyl-1,2,5-thiadiazolidin-2-yl]-1H-indole A solution of the product from Step 1 (880 mg) in 98% formic acid (20 ml) was allowed to stand at room temperature for 30 minutes. The solvent was then removed under vacuum (bath temperature 30° C.) and the residue was azeotroped with a mixture of toluene (30 ml) and methanol (10 ml) to give a pale brown thick oil. Flash chromatography of the crude mixture (silica gel, dichloromethane-methanol-ammonia, 80:20:2) gave 450 mg (67.8%) of the title compound as a colourless thick oil; $\delta_H$(250 MHz, CDCl$_3$) 8.15 (1H, br s, indole N—H), 7.57 (1H, s, Ar—H), 7.34 (1H, d, J=8.4 Hz, Ar—H), 7.21 (1H, dd, J=8.4 and 1.6 Hz, Ar—H), 7.06 (1H, d, J=2.1 Hz, Ar—H), 4.31 (2H, s, Ar—CH$_2$—N), 3.28—3.12 (4H, m, —NCH$_2$CH$_2$N—), 3.03 (2H, t, J=6.0 Hz, —CH$_2$—), 2.90 (2H, t, J=6.0 Hz, —CH$_2$—), 2.78 (3H, s, —NMe); m/z (CI) 309 (M+ +1).

Method B

1.
5-Methyl-2-(4-nitrobenzyl)-1,2,5-thiadiazolidine-1,1-dioxide

To a stirred suspension of anhydrous potassium carbonate (14.49 g, 104.8 mmol) in anhydrous dimethylformamide (80 ml) was added dropwise over 4 minutes a solution of 2-methyl-1,2,5-thiadiazolidine-1,1-dioxide (14 g, 102.8 mmol) in anhydrous dimethylformamide (40 ml), under nitrogen. After 5 minutes, solid 4-nitrobenzyl bromide (22.43 g, 103.8 mmol) was added in one portion and stirring was continued at room temperature for 5 hours. Water (200 ml) was added and products were extracted into ethyl acetate (3×150 ml). The combined organic phases were washed with brine (1×50 ml), dried (Na$_2$SO$_4$) and concentrated. The crude residue was crystallized from ethyl acetate-hexane (70:30) to give 18.31 g (67%) of the title compound as pale yellow crystals. Purification of the mother liquors by flash chromatography (silica gel, hexane-ethyl acetate, 30:70) afforded a further 5.1 g (18.2%) of required product; mp 105°-107° C.; $\delta_H$ (250 MHz, CDCl$_3$) 8.22 (2H, d, J=8.7 Hz, Ar—H), 7.57 (2H, d, J=8.7 Hz, Ar—H), 4.32 (2H, s, Ar—CH$_2$—), 3.36—3.21 (4H, m, N—CH$_2$CH$_2$—N), 2.80 (3H, s, —NMe); m/z (CI) 270 (M+-1).

2.
2-(4-Aminobenzyl)-5-methyl-1,2,5-thiadiazolidine-1,1-dioxide. Hydrochloride A suspension of the product from Step 1 (20 g, 74.72 mmol) in a mixture of absolute ethanol (300 ml), ethyl acetate (150 ml), 2N hydrochloric acid (39 ml) and water (25 ml), was hydrogenated at 30 psi for 7 minutes over 10% palladium on carbon (2 g). The catalyst was removed by filtration, washed with ethanol (2×30 ml) and solvents were removed under vacuum. The remaining residue was azeotropically dried with absolute ethanol (1×150 ml) and further dried at high vacuum to give 20.36 g (99.5%) of the required title compound as a white solid. A sample recrystallised from absolute ethanol showed: mp 153°-156° C. (white needles); $\delta_H$ (250 MHz, DMSO-d$_6$) 7.42 (2H, d, J=8.4 Hz, Ar—H), 7.29 (2H, d, J=8.4 Hz, Ar—H), 4.15 (2H, s, Ar—CH$_2$—N), 3.27—3.17 (4H, m, N—CH$_2$CH$_2$—N), 2.62 (3H, s, —NMe); m/z (CI) 240 (M+-1).

3.
4-[(1,1-Dioxo-5-methyl-1,2,5-thiadiazolidin-2-yl)methyl]-phenylhydrazine To a cooled (−10° C.) and stirred suspension of the product from Step 2 (20 g, 72.0 mmol) in concentrated hydrochloric acid (100 ml) and water (10 ml) was added dropwise a solution of sodium nitrite (5.22 g, 75.6 mmol) in water (40 ml) at such a rate as to maintain the temperature below −5° C. (ca 20 minutes). After a further 10 minutes, the mixture was quickly filtered to remove solids and the filtrate was added portionwise to a cooled (−15° C.) and stirred solution of tin (II) chloride dihydrate (81.2 g, 360 mmol) in concentrated hydrochloric acid (60 ml) at such a rate as to maintain the temperature below −10° C. (ca 15 minutes). The mixture was allowed to warm to 0° C. and it was concentrated to 50% of the volume under vacuum. The remaining acid aqueous solution was basified with 10N potassium hydroxide (temperature maintained below 30° C.) and the resulting mixture was shaken with ethyl acetate (500 ml) and filtered through Hyflo supercel filter aid. The organic phase was decanted off and the basic aqueous solution was extracted with ethyl acetate (3×250 ml). The combined organic phases were washed with brine (1×100 ml), dried (Na$_2$SO$_4$) and concentrated. Crystallization of the remaining residue from ethyl acetate followed by flash chromatography purification of the mother liquors (silica gel, ethyl acetate-methanol, 98:2; and dichloromethane-methanol, 95:5) gave 6.5 g (35%) of the required title compound as a yellow solid; $\delta_H$(250 MHz, DMSO-d$_6$) 7.07 (2H, d, J=8.5 Hz, Ar—H), 6.74 (2H, d, J=8.5 Hz, Ar—H), 6.70 (1H, br s, —NH—), 3.94 (2H, s, Ar—CH$_2$—N), 3.91 (2H, br s, —NH$_2$), 3.23—3.05 (4H, m, N—CH$_2$CH$_2$—N), 2.60 (3H, s, —NMe); m/z (EI) 256 (M+).

4.
3-(2-Aminoethyl)-5-[(1,1-dioxo-5-methyl-1,2,5-thiadiazolidin-2-yl)methyl]-1H-indole To a stirred solution of the product from Step 3 (3.0 g, 11.70 mmol) in a mixture of absolute ethanol (100 ml), water (15 ml) and 2N hydrochloric acid (5.85 mL, 11.70 mmol) was added 4-chlorobutanal dimethylacetal (1.78 g, 11.70 mmol) and the resulting solution was refluxed for 2 hours. The solvent was removed under vacuum and the residue was azeotroped dried with absolute ethanol (50 ml). The remaining residue was heated with absolute ethanol (100 ml) and the solvent was decanted off from the dark residual solid. The solution was allowed to cool to room temperature and it was filtered again before solvents were removed under vacuum. Flash chromatography (silica gel, dichloromethane-methanol-ammonia, 90:10:1) of the residue gave 288 mg (8%) of the title compound; the spectroscopic properties of this material were identical to those of the compound prepared using Method A.

EXAMPLE 2

3-[2-(Dimethylamino)ethyl]-5-[(1,1-dioxo-5-methyl-1,2,5-thiadiazolidin-2-yl)methyl]-1H-indole. Succinate To a cooled (−5° C.) and stirred solution of 3-(2-aminoethyl)-5-[(1,1-dioxo-5-methyl -1,2,5-thiadiazolidin-2-yl)methyl]-1H-indole (440 mg, 1.42 mmol) (Example 1) in methanol (20 ml) and glacial acetic acid (0.4 mL, 7.10 mmol) was added sodium cyanoborohydride (196 mg, 3.12 mmol) followed by dropwise addition of a solution of formaldehyde (38% aqueous solution; 0.41 ml) in methanol (5 ml) over 5 minutes. The resulting solution was stirred at $-5°$ C. for 20 minutes and at room temperature for 1 hour before saturated aqueous potassium carbonate (19 ml) was added and the methanol was removed under vacuum. The aqueous residue was diluted with water (5ml) and extracted with ethyl acetate (2×70 ml), washed with brine (2×40 ml), dried (MgSO$_4$) and concentrated. Flash chromatography of the crude product (silica gel, dichloromethane-methanol-ammonia, 90:10:1; and diethyl ether-methanol-ammonia, 70:30:1.6) afforded 376 mg (78.8%) of the title compound free base as a colourless thick oil. The succinate salt was prepared and recrystallised from ethanol-diethyl ether; mp 178°-181° C.; $\delta_H$ (360 MHz, DMSO-d$_6$) 10.85 (1H, s, indole N—H), 7.51 (1H, s, Ar—H), 7.32 (1H, d, J=8.3 Hz, Ar—H), 7.18 (1H, d, J=1.8 Hz, Ar—H), 7.07 (1H, dd, J=8.3 and 1.4 Hz, Ar—H), 4.17 (2H, s, Ar—CH$_2$—N), 3.22 (2H, t, J=6.1 Hz, —CH$_2$—), 3.13 (2H, t, J=6.1 Hz, —CH$_2$—), 2.87 (2H, t, J=6.9 Hz, —CH$_2$—), 2.72 (2H, t, J=6.9 Hz, —CH$_2$), 2.63 (3H, s, —NMe), 2.38 (6H, s, —NMe$_2$), 2.31 (4H, s, succinic acid); m/z (CI) 337 (M$^+$+1). (Found: C, 52.71; H, 6.92; N, 12.02. C$_{16}$H$_{24}$N$_4$O$_2$S×1.0 C$_4$H$_6$O$_4$ requires: C, 52.85; H, 6.65; N, 12.33%).

EXAMPLE 3

3-(2-Aminoethyl)-5-[2-(1,1-dioxo-5-methyl-1,2,5-thiadiazolidin-2-yl)ethyl]-1H-indole

1.

3-[2-(N-Tert-butyloxycarbonylamino)ethyl]-5-[2-(1,1-dioxo-5-methyl-1,2,5-thiadiazolidin-2-yl)ethyl]-1H-indole The title compound was prepared from Intermediate 2 and 2-methyl-1,2,5-thiadiazolidine-1,1-dioxide by a similar method to that described for Example 1 (Step 1) as a colourless thick oil; $\delta_H$ (250 MHz, CDCl$_3$) 8.02 (1H, br s, indole N—H), 7.44 (1H, s, Ar—H), 7.30 (1H, d, J=8.3 Hz, Ar—H), 7.07 (1H, dd, J=8.3 and 1.6 Hz, Ar—H), 7.02 (1H, d, J=2.2 Hz, Ar—H), 4.61 (1H, br s, —NH—), 3.44 (2H, br q, J=6.8 Hz —CH$_2$—NH—), 3.36 (2H, dd, J=8.3 and 5.7 Hz, —CH$_2$N—), 3.29—3.24 (4H, m, —N CH$_2$CH$_2$N—), 3.05 (2H, dd, J=8.3 and 5.7 Hz, —CH$_2$—), 2.93 (2H, t, J=6.8 Hz, Ar—CH$_2$CH$_2$NH—), 2.75 (3H, s, —NMe), 1.43 (9H, s, t-Bu); m/z (EI) 422 (M$^+$). (Found: m/z 422.1971. C$_{20}$H$_{30}$N$_4$O$_4$S requires: m/z 422.1988).

2.

3-(2-Aminoethyl)-5-[2-(1,1-dioxo-5-methyl-1,2,5-thiadiazolidin-2-yl)ethyl]-1H-indole A solution of the product from Step 1 (916 mg) in anhydrous dichloromethane (15 ml) and trifluoroacetic acid (4.5 ml) was stirred at room temperature under a nitrogen atmosphere for 1 hour. Solvents were removed under vacuum and the residue was azeotroped with toluene-methanol. Flash chromatography of the crude product (silica gel, dichloromethane-methanol-ammonia, 90:10:1) gave 372 mg (59%) of the title compound as a colourless thick oil which solidified on standing; $\delta_H$ (250 MHz, CDCl$_3$) 8.16 (1H, br s, indole N—H), 7.45 (1H, s, Ar—H), 7.28 (1H, d, J=8.3 Hz, Ar—H), 7.05 (1H, dd, J=8.3 and 1.5 Hz, Ar—H), 7.02 (1H, d, J=1.8 Hz, Ar—H), 3.35 (2H, dd, J=9.8 and 7.1 Hz, —CH$_2$N—), 3.26 (4H, s, —NCH$_2$CH$_2$N—), 3.08—2.99 (4H, m, —CH$_2$—), 2.88 (2H, t, J=6.2 Hz, Ar—CH$_2$CH$_2$NH$_2$), 2.75 (3H, s, —NMe); m/z (CI) 323 (M$^+$+1). (Found: m/z 323.1543. C$_{15}$H$_{23}$N$_4$O$_2$S requires: m/z 323.1542).

EXAMPLE 4

3-[2-(Dimethylamino)ethyl]-5-[2-(1,1-dioxo-5-methyl-1,2,5-thiadizolidin-2-yl)ethyl]-1H-indole. Oxalate The title compound was prepared in 81% yield from 3-(2-aminoethyl)-5-[2-(1,1-dioxo-5-methyl-1,2,5-thiadiazolidin-2-yl)ethyl]-1H-indole (Example 3) following the conditions described for Example 2. The oxalate salt was prepared and recrystallised from methanol-diethyl ether; mp 137°-139° C.; $\delta_H$ (360 MHz, DMSO-d$_6$) 10.88 (1H, s, indole N—H), 7.45 (1H, s, Ar—H), 7.29 (1H, d, J=8.2 Hz, Ar—H), 7.20 (1H, s, Ar—H), 7.00 (1H, d, J=8.2 Hz, Ar—H), 3.34-3.30 (2H, m, —CH$_2$—), 3.28-3.16 (6H, m, —CH$_2$—), 3.06-3.01 (2H, m, —CH$_2$—), 2.95-2.90 (2H, m, —CH$_2$—), 2.79 (6H, s, —NMe$_2$), 2.60 (3H, s, —NMe); m/z (EI) 350 (M$^+$). (Found: C, 51.51; H, 6.47; N, 12.53. C$_{17}$H$_{26}$N$_4$O$_2$S×1.0 C$_2$H$_2$O$_4$ requires: C, 51.80; H, 6.41; N, 12.72%).

EXAMPLE 5

3-(2-Aminoethyl)-5-[(5-(4-acetylamino)benzyl-1,1-dioxo-1,2,5-thiadiazolidin-2-yl)methyl]-1-indole

1.

2-Tert-butyl-5-(4-nitrobenzyl)-1,2,5-thiadiazolidine-1,1-dioxide

The title compound was prepared in 70% yield from 2-tert-butyl-1,2,5-thiadiazolidine-1,1-dioxide [M. Preiss, Chem. Ber., 1978, 111, 1915] and 4-nitrobenzyl bromide following the procedure described for Example 1 (Method B, Step 1); mp 113° C. (ethyl acetate-hexane, 60:40); $\delta_H$(360 MHz, CDCl$_3$) 8.21 (2H, d, J=8.7 Hz, Ar—H), 7.58 (2H, d, J=8.7 Hz, Ar—H), 4.24 (2H, s, Ar—CH$_2$—), 3.40 (2H, t, J=6.2 Hz, —CH$_2$—), 3.17 (2H, t, J=6.2 Hz, —CH$_2$—), 1.44 (9H, t-Bu); m/z (EI) 313 (M$^+$).

2. 2-(4-Nitrobenzyl)-1,2,5-thiadiazolidine-1,1dioxide

A solution of the product from Step 1 (1.5 g) in anhydrous dichloromethane (10 ml) and trifluoroacetic acid (10 ml) was allowed to stand at room temperature for 48 hours. Solvents were removed under vacuum and the remaining residue was azeotroped with methanol (1×25 ml) and crystallised from ethyl acetate-hexane to give 966 mg (78%) of the title compound as a pale yellow solid; mp 115°-117° C.; $\delta_H$ (250 MHz, CDCl$_3$) 8.23 (2H, d, J=8.8 Hz, Ar—H), 7.57 (2H, d, J=8.8 Hz, Ar—H), 4.38 (1H, br t, —NH—), 4.29 (2H, s, Ar—CH$_2$—), 3.54 (2H, q, J=6.6 Hz, —CH$_2$—NH—), 3.34 (2H, t, J=6.6 Hz, —CH$_2$—).

3.

3-[2-(N-Tert-butyloxycabornylamino)ethyl]-5-[(1,1-dioxo-5-(4-nitrobenzyl)-1,2,5-thiadiazolidin-2-yl)methyl]-1H-indole To a stirred solution of Intermediate 1 (920 mg, 3.17 mmol), 2-(4-nitrobenzyl)-1,2,5-thiadiazolidine-1,1dioxide (900 mg, 3.49 mmol) and triphenylphosphine (914 mg, 3.49 mmol) in anhydrous tetrahydrofuran (25 ml) was added dropwise over 13 minutes diethyl azodicarboxylate (549 µL, 3.49 mmol) under a nitrogen atmosphere. After being stirred at room temperature for 4.5 hours, solvents were removed under vacuum and the remaining residue was purified three times by flash chromatography (silica gel, dichloromethane-ethanol, 97:3; diethyl ether; and hexane-ethyl acetate, 40:60) to give 793 mg (47.2%) of the title compound as a yellow foam; $\delta_H$ (250 MHz, CDCl$_3$) 8.22 (2H, d, J=8.8 Hz, Ar—H), 8.10 (1H, br s, indole N—H), 7.58 (2H, d, J=8.8 Hz, Ar—H), 7.56 (1H, s, Ar—H), 7.36 (1H, d, J=8.4 Hz, Ar—H), 7.23 (1H, dd, J=8.4 and 1.6 Hz, Ar—H), 7.06 (1H, d, J=2.1 Hz, Ar—H), 4.61 (1H, br s, —NH—), 4.35 (2H, s, Ar—CH$_2$—), 4.34 (2H, s, Ar—CH$_2$—), 3.45 (2H, br q, J=6.9 Hz, —CH$_2$NH—), 3.19 (4H, s, —NCH$_2$CH$_2$N—), 2.95 (2H, t, J=6.9 Hz, Ar—CH$_2$CH$_2$NH—), 1.43 (9H, s, t-Bu).

4.

3-[2-(N-Tert-butyloxycarbonylamino)ethyl]-5-[(5-(4-acetylamino)benzyl-1,1-dioxo-1,2,5-thiadiazolidin-2-yl)methyl]-1H-indole A solution of the product from Step 3 (780 mg, 1.47 mmol) in a mixture of absolute ethanol (30 ml) and 2N hydrochloric acid (0.74 ml) was hydrogenated over palladium on carbon (10%; 108 mg) at 30 psi for 10 minutes. The catalyst was removed by filtration, washed with absolute ethanol (2×10 ml) and solvents were removed under vacuum. The remaining residue, after being azeotroped with a mixture of toluene (30 ml) and methanol (10 ml), was dissolved in anhydrous dichloromethane (20 ml) and treated with anhydrous triethylamine (0.61 ml, 4.41 mmol) followed by acetic anhydride (0.20 mL, 2.20 mmol). After being stirred at room temperature for 1.5 hours, 1N hydrochloric acid (30 ml) was added and the products were extracted into ethyl acetate (2×75 ml). The combined organic extracts were washed with brine (1×40 ml), dried (MgSO$_4$) and concentrated. Flash chromatography of the residue (silica gel, hexane-ethyl acetate, 20:80) gave 684 mg (86%) of the title compound as a white foam; $\delta_H$(250 MHz, CDCl$_3$) 8.12 (1H, br s, indole N—H), 7.54 (1H, s, Ar—H), 7.49 (2H, d, J=8.4 Hz, Ar—H), 7.38 (1H, br s, Ar—NHCO—), 7.34 (1H, d, J=8.2 Hz, Ar—H), 7.33 (2H, d, J=8.4 Hz, Ar—H), 7.21 (1H, dd, J=8.2 and 1.6 Hz, Ar—H), 7.05 (1H, d, J=2.2 Hz, Ar—H), 4.63 (1H, br s, —NH—), 4.31 (2H, s, Ar—CH$_2$—), 4.20 (2H, s, Ar—CH$_2$—), 3.45 (2H, br q, J=6.8 Hz, —CH$_2$NH—), 3.11 (4H, m, —NCH$_2$CH$_2$N—), 2.94 (2H, t, J=6.8 Hz, Ar—CH$_2$CH$_2$NH—), 2.17 (3H, s, CH$_3$CO—), 1.43 (9H, s, t-Bu).

5.

3-(2-Aminoethyl)-5-[(5-(4-acetylamino)benzyl-1,1-dioxo-1,2,5-thiadiazolidin-2-yl)methyl]-1H-indole The title compound was prepared in 67% yield from 3-[2-(N-tert-butyloxycarbonylamino)ethyl]-5-[5-(4-acetylamino)benzyl-1,1-dioxo-1,2,5-thiadiazolidin-2-yl)methyl]-1H-indole (Step 4) by a similar method to that described in Example 1 (Step 2) as a white foam; $\delta_H$(360 MHz, CDCl$_3$), 8.14 (1H, br s, indole N-H), 7.56 (1H, s, Ar-H), 7.48 (2H, d, J=8.4 Hz, Ar-H), 7.46 (1H, br s, ArNHCO-), 7.33 (3H, d, J=8 Hz, Ar-H), 7.20 (1H, dd, J=8.3 and 1.5 Hz, Ar-H), 7.05 (1H, d, J=2.1 Hz, Ar-H), 4.31 (2H, s, Ar-CH$_2$-), 4.20 (2H, s, Ar-CH$_2$-), 3.10 (4H, s, -NCH$_2$CH$_2$N-), 3.03 (2H, t, J=6.4 Hz, -CH$_2$-), 2.90 (2H, t, J=6.4 Hz, -CH$_2$-), 2.17 (3H, s, CH$_3$CO-).

EXAMPLE 6

3-[2-(Dimethylamino)ethyl]-5-[(5-(4-acetylamino)benzyl-1,1-dioxo-1,2,5-thiadiazolidin-2-yl)methyl]-1H-indole. Succinate The title compound free base was prepared in 78% yield from 3-(2-aminoethyl)-5-[5-(4-acetylamino)benzyl-1,1-dioxo-1,2,5-thiadiazolidin-2-yl)methyl]-1H-indole (Example 5) following the conditions described for Example 2. The crude product was purified by flash chromatography (silica gel, dichloromethane-methanol-ammonia, 90:10:1.2) and the succinate salt was prepared and recrystallised from ethanoldiethyl ether; mp 158°–161° C., $\delta_H$(360 MHz, DMSO-d$_6$) 10.86 (1H, s, indole N—H), 9.94 (1H, s, ArNHCO—), 7.55 (2H, d, J=8.5 Hz, Ar—H), 7.52 (1H, s, Ar—H), 7.32 (1H, d, J=8.3 Hz, Ar—H), 7.28 (2H, d, J=8.5 Hz, Ar—H), 7.18 (1H, s, Ar—H), 7.07 (1H, dd, J=8.3 and 1.5 Hz, Ar—H), 4.18 (2H, s, Ar—CH$_2$—), 4.07 (2H, s, Ar—CH$_2$—), 3.12 (4H, s, —NCH$_2$CH$_2$N—), 2.87 (2H, br t, J=8 Hz, —CH$_2$—), 2.73 (2H, br t, J=8 Hz, —CH$_2$—), 2.38 (6H, s, —NMe$_2$), 2.36 (4H, s, succinic acid), 2.03 (3H, s, CH$_3$CO—).

Examples 7 and 8 were prepared from Intermediate 1 and the appropriate 1,2,5-thiadiazolidine-1,1-dioxide [V.P. Arya, K. Nagarajan, S. J. Shenoy, *Indian J. Chem.*, 1982, 21B, 941; *M. Preiss, Chem. Ber.*, 1978, 111, 1915] using a similar method to that described for Example 1 (Method A).

EXAMPLE 7

3-(2-Aminoethyl)-5-[(1,1-dioxo-1,2,5-thiadiazolidin-2-yl)methyl]-1H-indole

1.

3-[2-(N-Tert-butyloxycarbonylamino)ethyl]-5-[(1,1-dioxo-1,2,5-thiadiazolidin-2-yl)methyl]-1H-indole White foam; $\delta_H$ (250 MHz, CDCl$_3$) 8.11 (1H, br s, indole N—H), 7.57 (1H, s, Ar—H), 7.35 (1H, d, J=8.3 Hz, Ar—H), 7.21 (1H, dd, J=8.3 and 1.5 Hz, Ar—H), 7.06 (1H, d, J=2.2 Hz, Ar—H), 4.62 (1H, br s, —NH—), 4.43 (1H, br s, —NH—), 4.29 (2H, s, Ar—CH$_2$N—), 3.44 (4H, br q, —CH$_2$NHBOC and —CH$_2$—), 3.27 (2H, t, J=6.8 Hz, —CH$_2$—), 2.94 (2H, t, J=6.9 Hz, Ar—CH$_2$CH$_2$N—), 1.43 (9H, s, t-Bu); m/z (EI) 394 (M+). (Found: m/z 394.1644. C$_{18}$H$_{26}$N$_4$O$_4$S requires: m/z 394.1675).

2.

3-(2-Aminoethyl)-5-[(1,1-dioxo-1,2,5-thiadiazolidin-2-yl)methyl]-1H-indole

Colourless thick oil; $\delta_H$(250 MHz, CDCl$_3$—CD$_3$OD) 7.54 (1H, s, Ar—H), 7.33 (1H, d, J=8.4 Hz, Ar—H), 7.15 (1H, dd, J=8.4 and 1.6 Hz, Ar—H), 7.05 (1H, s, Ar—H), 4.24 (2H, s, Ar—CH$_2$N—), 3.43–3.39 (2H, m, —CH$_2$—), 3.25–3.19 (2H, m, —CH$_2$—), 3.00–2.85 (4H, m, Ar—CH$_2$CH$_2$N—).

EXAMPLE 8

3-(2-Aminoethyl)-5-[(1,1-dioxo-5-isopropyl-1,2,5-thiadiazolidin-2-yl)methyl]-1H-indole 1.3-[2-(N-Tert-butyloxycarbonylamino)ethyl]-5-[(1,1-dioxo-5-isopropyl-1,2,5-thiadiazolidin-2-yl)methyl]-1H-indole Colourless thick oil; $\delta_H$ (250 MHz, CDCl$_3$) 8.14 (1H, br s, indole N—H), 7.54 (1H, s, Ar—H), 7.33 (1H, d, J=8.3 Hz, Ar—H), 7.21 (1H, dd, J=8.3 and 1.6 Hz, Ar—H), 7.04 (1H, d, J=2.2 Hz, Ar—H), 4.61 (1H, br, s, —NH—), 4.26 (2H, s, Ar—CH₂N—), 3.77 (1H, m, 6.6 Hz, —CH—), 3.44 (2H, br q, —CH₂NH—), 3.28—3.23 (2H, m, —CH₂—), 3.16–3.10 (2H, m, —CH₂—), 2.94 (2H, t, J=6.9 Hz, Ar—CH₂CH₂N—), 1.43 (9H, s, t-Bu), 1.29 (6H, d, J=6.6 Hz, Me₂CH—); m/z (EI) 437 (M⁺+1).

2.

3-(2-Aminoethyl)-5-[(1,1-dioxo-5-isopropyl-1,2,5-thiadiazolidin-2-yl)methyl]-1H-indole Colourless thick oil; $\delta_H$ (360 MHz, CDCl₃) 8.25 (1H, br s, indole N—H), 7.55 (1H, s, Ar—H), 7.32 (1H, d, J=8.3 Hz, Ar—H), 7.18 (1H, br d, J=8.3 Hz, Ar—H), 7.05 (1H, s, Ar—H), 4.25 (2H, s, Ar—CH₂N—), 3.73 (1H, m, J=6.6 Hz, —CH—), 3.24 (2H, t, J=6.4 Hz, —CH₂—), 3.13 (2H, t, J=6.4 Hz, —CH₂—), 3.02 (2H, m, —CH₂—), 2.90 (2H, m, —CH₂—), 1.29 (6H, d, J=6.6 Hz, Me₂CH—), m/z (CI) 337 (M⁺+1).

Examples 9 and 10 were prepared from Intermediate 2 and the appropriate 1,2,5-thiadiazolidine-1,1-dioxide following the procedure described for Example 1 (Method A).

EXAMPLE 9

3-(2-Aminoethyl)-5-[2-(1,1-dioxo-1,2,5-thiadiazolidin-2-yl)ethyl]-1H-indole

1.

3-[2-(N-Tert-butyloxycarbonylamino)ethyl]-5-[2-(1,1-dioxo-1,2,5-thiadiazolidin-2-yl)ethyl]-1H-indole The title compound was isolated in 5% yield as a white solid; $\delta_H$ (250 MHz, CDCl₃) 8.00 (1H, br s, indole N—H), 7.53 (1H, s, Ar—H), 7.30 (1H, d, J=8.3 Hz, Ar—H), 7.06 (1H, dd, J=8.3 and 1.5 Hz, Ar—H), 7.02 (1H, d, J=2.2 Hz, Ar—H), 4.62 (2H, br s, —NH—), 3.50—3.30 (4H, m, —CH₂—), 3.07 (2H, t, J=8.2 Hz, —CH₂—), 2.94 (2H, t, J=6.8 Hz, Ar—CH₂CH₂NH—), 1.43 (9H, s, t-Bu).

2.

3-(2-Aminoethyl)-5-[2-(1,1-dioxo-1,2,5-thiadiazolidin-2-yl)ethyl]-1H-indole

White solid; $\delta_H$ (360 MHz, DMSO-d₆) 7.37 (1H, s, Ar—H), 7.25 (1H, d, J=8.3 Hz, Ar—H), 7.08 (1H, d, J=2.0 Hz, Ar—H), 6.95 (1H, dd, J=8.3 and 1.4 Hz, Ar—H), 3.27 (4H, m, —CH₂—), 3.10 (2H, t, J=8.3 Hz, —CH₂—), 2.90 (2H, t, J=8.3 Hz, —CH₂—), 2.60 (2H, m, —CH₂—), 2.71 (2H, m, —CH₂—); m/z (CI) 309 (M⁺+1).

EXAMPLE 10

3-(2-Aminoethyl)-5-[2-(1,1-dioxo-5-ethyl-1,2,5-thiadiazolidin-2-yl)ethyl]-1H-indole

1.

3-[2-(N-Tert-butyloxycarbonylamino)ethyl]-5-[2-(1,1-dioxo-5-ethyl-1,2,5-thiadiazolidin-2-yl)ethyl]-1H-indole The title compound was isolated in 56% yield as a white solid; $\delta_H$ (360 MHz, CDCl₃) 8.00 (1H, br s, indole N—H), 7.44 (1H, s, Ar—H), 7.30 (1H, d, J=8.3 Hz, Ar—H), 7.07 (1H, dd, J=8.3 and 1.4 Hz, Ar—H), 7.02 (1H, s, Ar—H), 4.62 (1H, br s, —NH—), 3.45 (2H, m, —CH₂NH—), 3.33 (2H, dd, J=8.5 and 5.8 Hz, —CH₂N—), 3.27 (4H, s, —NCH₂CH₂N—), 3.11 (2H, q, J=7.3 Hz, CH₃CH₂N—), 3.05 (2H, dd, J=8.5 and 5.8 Hz, —CH₂—), 2.93 (2H, t, J=6.8 Hz, Ar—CH₂CH₂NH—), 1.43 (9H, s, t-Bu), 1.26 (3H, t, J=7.3 Hz, —CH₃).

2.

3-(2-Aminoethyl)-5-[2-(1,1-dioxo-5-ethyl-1,2,5-thiadiazolidin-2-yl)ethyl]-1H-indole White solid; $\delta_H$ (360 MHz, CDCl₃) 8.07 (1H, br s, indole N—H), 7.45 (1H, s, Ar—H), 7.28 (1H, d, J=8.3 Hz, Ar—H), 7.05 (1H, dd, J=8.3 and 1.4 Hz, Ar—H), 7.04 (1H, s, Ar—H), 3.36–3.24 (6H, m, —CH₂—), 3.13–3.02 (6H, m, —CH₂—), 2.93 (2H, t, J=6.4 Hz, —CH₂—), 1.26 (3H, t, J=7.3 Hz, —CH₃).

Examples 11–14 were prepared from the products of Examples 7–10 using a similar method to that described for Example 2.

EXAMPLE 11

3-[2-(Dimethylamino)ethyl]-5-[(1,1-dioxo-1,2,5-thiadiazolidin-2-yl)methyl]-1H-indole. Succinate The succinate salt was prepared and recrystallized from ethanol-diethyl ether; mp 159°–161° C.; $\delta_H$ (360 MHz, DMSO-d₆) 10.85 (1H, s, indole N—H), 7.49 (1H, s, Ar—H), 7.31 (1H, d, J=8.4 Hz, Ar—H), 7.10 (2H, br s, Ar—H and —NH—), 7.06 (1H, dd, J=8.4 and 1.5 Hz, Ar—H), 4.09 (2H, s Ar—CH₂N—), 3.24 (2H, br q, J=6.5 Hz, —CH₂NH—), 3.15 (2H, t, J=6.5 Hz, —HNCH₂CH₂N—), 2.87 (2H, br t, J=8.4 Hz, —CH₂—), 2.73 (2H, br t, J=8.4 Hz, —CH₂—), 2.38 (6H, s, —NMe₂), 2.36 (4H, s, succinic acid); m/z (CI) 323 (M⁺+1). (Found: C, 52.05; H, 6.10; N, 12.40. C₁₅H₂₂N₄O₂S×1.0 C₄H₆O₄ requires: C, 51.80; H, 6.41; N, 12.72%).

EXAMPLE 12

3-[2-(Dimethylamino)ethyl]-5-[(1,1-dioxo-5-isopropyl-1,2,5-thiadiazolidin-2-yl)methyl]-1H-indole. Oxalate The oxalate salt was prepared and recrystallised from ethanol-diethyl ether; mp 186°–187° C.; $\delta_H$ (360 MHz, DMSO-d₆) 11.00 (1H, s, indole N—H), 7.56 (1H, s, Ar—H), 7.36 (1H, d, J=8.3 Hz, Ar—H), 7.25 (1H, s, Ar—H), 7.10 (1H, d, J=8.3 Hz, Ar—H), 4.12 (2H, s, Ar—CH₂N—), 3.54 (1H, m, J=6.6 Hz, —CH—), 3.29-3.21 (4H, m, —CH₂—), 3.12–3.00 (4H, m, —CH₂—), 2.80 (6H, s, —NMe₂), 1.19 (6H, d, J=6.6 Hz, Me₂CH—); m/z (EI) 364 (M⁺). (Found: C, 52.59; H, 6.55; N, 12.23. C₁₈H₂₈N₄O₂S×1.0 C₂H₂O₄ requires: C, 52.85; H, 6.65; N, 12.33%).

EXAMPLE 13

3-[2-(Dimethylamino)ethyl]-5-[2-(1,1-dioxo-1,2,5-thiadiazolidin-2-yl)ethyl]-1H-indole. Oxalate The oxalate salt was prepared and recrystallised from ethanol-diethyl ether; mp 154°–155° C.; $\delta_H$ (360 MHz, D₂O) 7.57 (1H, s, Ar—H), 7.48 (1H, d, J=8.4 Hz, Ar—H), 7.32 (1H, s, Ar—H), 7.19 (1H, dd, J=8.4 and 1.3 Hz, Ar—H), 3.50–3.42 (6H, m, —CH₂—), 3.37 (2H, t, J=7.0 Hz, —CH₂—), 3.23 (2H, t, J=7.3 Hz, —CH₂—), 3.05 (2H, t, J=7.0 Hz, —CH₂—), 2.90 (6H, s, —NMe₂); m/z (CI) 337 (M⁺+1). (Found: C, 50.60; H, 5.79; N, 12.78. C₁₆H₂₄N₄O₂S×1.0 C₂H₂O₄ requires: C, 50.69; H, 6.15; N, 13.14%).

EXAMPLE 14

3-[2-(Dimethylamino)ethyl]-5-[2-(1,1-dioxo-5-ethyl-1,2,5-thiadiazolidin-2-yl)ethyl]-1H-indole. Succinate The succinate salt was prepared and recrystallised from ethanol-diethyl ether; mp 144°-145° C.; $\delta_H$ (360 MHz, $D_2O$) 7.57 (1H, s, Ar—H), 7.49 (1H, d, J=8.4 Hz, Ar—H), 7.33 (1H, s, Ar—H), 7.19 (1H, dd, J=8.4 and 1.4 Hz, Ar—H), 3.49 (2H, t, J=7.3 Hz, —$CH_2$—), 3.42-3.31 (6H, m, —$CH_2$—), 3.24 (2H, t, J=7.3 Hz, —$CH_2$—), 3.10-3.03 (4H, m, —$CH_2$—), 2.91 (6H, s, —$NMe_2$), 2.52 (4H, s, succinic acid), 1.20 (3H, t, J=7.3 Hz, $CH_3$—); m/z (EI) 364 (M+). (Found: C, 53.99; H, 6.95; N, 11.23. $C_{18}H_{28}N_4O_2Sx$ 1.0 $C_4H_6O_4 \times 0.3H_2O$ requires: C, 54.15; H, 7.15; N, 11.48%).

EXAMPLE 15

3-[2-(Methylamino)ethyl]-5-[(1,1-dioxo-5-methyl-1,2,5-thiadiazolidin-2-yl)methyl]-1H-indole. Succinate.

1.3-[2-(N-Formylamino)ethyl]-5-hydroxymethyl-1H-indole

To a cooled (−70° C.) and stirred solution of ethyl 3-[2-(N-tert-butyloxycarbonylamino)ethyl]-1H-indole-5-carboxylate (Intermediate 1, step 3) (5.2 g, 15.6 mmol) in anhydrous tetrahydrofuran (250 ml) was added dropwise, under nitrogen, diisobutylaluminium hydride (1M in toluene; 65.7 ml) over 15 minutes. The mixture was then allowed to warm to 0° C. and it was stirred for 2 hours before the excess of diisobutylaluminium hydride was destroyed by dropwise addition of anhydrous methanol (25 ml) at −50° C. Aqueous citric acid (10%; 200 ml) was added, the mixture was diluted with ethyl acetate (200 ml) and the organic phase was decanted off, washed with brine (50 ml), dried ($MgSO_4$) and concentrated. Flash chromatography (silica gel, dichloromethane-methanol 96:4 to 90:10) of the residue gave 2.1 g of Intermediate 1 and 0.8 g of the title compound as a colourless thick oil; $\delta_H$ (360 MHz, DMSO-$d_6$) 10.73 (1H, s, indole N—H), 8.05 (1H, br s, —NHCHO), 8.02 (1H, s, —NCHO), 7.46 (1H, s, Ar—H), 7.27 (1H, d, J=8.3 Hz, Ar—H), 7.13 (1H, d, J=2.1 Hz, Ar—H), 7.04 (1H, dd, J=8.3 and 1.4 Hz, Ar—H), 4.95 (1H, t, J=5.6 Hz, —OH), 4.54 (2H, d, J=5.6 Hz, Ar—$CH_2OH$), 3.37 (2H, q, J=7.4 Hz, —$CH_2N$—), 2.82 (2H, t, J=7.4 Hz, Ar—$CH_2$—); m/z (EI) 218 (M+).

2.
3-[2-(N-Formylamino)ethyl]-5-[(1,1-dioxo-5-methyl-1,2,5-thiadiazolidin-2-yl)methyl]-1H-indole To a cooled (0° C.) and stirred solution of the product from step 1 (780 mg, 3.57 mmol), triphenylphosphine (1.13 g, 4.29 mmol) and 2-methyl-1,2,5-thiadiazolidine-1,1-dioxide (584 mg, 4.29 mmol) in anhydrous tetrahydrofuran (20 ml) was added dropwise, under nitrogen, diethyl azodicarboxylate (675 μl, 4.29 mmol) over 8 minutes. The mixture was allowed to warm to room temperature and it was stirred for 2 hours before anhydrous dimethylformamide (2 ml) was added and stirring was continued for a further 16 hours. Solvents were removed under vacuum and the residue was purified by flash chromatography (silica gel, dichloromethane-methanol 95:5; and ethyl acetate-methanol 99:1) to give 420 mg (40.8%) of the title compound as a colourless thick oil; $\delta_H$ (250 MHz, $CDCl_3$) 8.30 (1H, br s, indole N—H), 8.11 (1H, s, NCHO), 7.56 (1H, s, Ar—H), 7.34 (1H, d, J=8.4 Hz, Ar—$\overline{H}$), 7.19 (1H, dd, J=8.4 and 1.6 Hz, Ar—H), 7.05 (1H, d, J=2.4 Hz, Ar—H), 5.77 (1H, br s, —NH—), 4.30 (2H, s, Ar—$CH_2N$—), 3.62 (2H, q, J=6.6 Hz, —$CH_2NH$—), 3.28-3.16 (4H, m, —$CH_2$—), 2.98 (2H, t, J=6.6 Hz, Ar—$CH_2$—), 2.77 (3H, s, —NMe).

3.
3-[2-(Methylamino)ethyl]-5-[(1,1-dioxo-5-methyl-1,2,5-thiadiazolidin-2-yl)methyl]-1H-indole. Succinate To a cooled (0° C.) and stirred solution of the product from step 2 (440 mg, 1.31 mmol) in anhydrous tetrahydrofuran (10 ml) was added dropwise, under nitrogen, borane tetrahydrofuran complex (1M in tetrahydrofuran; 3.9 ml) over 3 minutes. The mixture was allowed to warm to room temperature and it was stirred for 6 hours before the excess of borane was destroyed by dropwise addition of methanol (4 ml). Solvents were removed under vacuum and the residue was dissolved in a mixture of 2N hydrochloric acid (25 ml) and methanol (25 ml) and it was allowed to stand at 30° C. for 20 minutes. The mixture was then basified with 2N aqueous sodium hydroxide (40 ml), the methanol was removed under vacuum and products were extracted with ethyl acetate (2×100 ml). The combined organic extracts were washed with brine (1×40 ml), dried ($Na_2SO_4$) and concentrated. Flash chromatography of the residue (silica gel, diethyl ether-methanol-ammonia 70:30:2.1) gave 100 mg (26%) of the required title compound free base as a thick oil. The succinate salt was prepared and recrystallised from ethanoldiethyl ether; mp 140°-142° C.; $\delta_H$ (360 MHz, DMSO-$d_6$) 10.95 (1H, br s, indole N—H), 7.53 (1H, s, Ar—H), 7.35 (1H, d, J=8.3 Hz, Ar—H), 7.23 (1H, s, Ar—H), 7.09 (1H, d, J=8.3 Hz, Ar—H), 4.17 (2H, s, Ar—$CH_2N$—), 3.24-3.20 (2H, m, —$CH_2$—), 3.16-3.12 (2H, m, —$CH_2$—), 3.06 (2H, t, J=7.6 Hz, —$CH_2$—), 2.95 (2H, t, J=7.6 Hz, —$CH_2$—), 2.62 (3H, s, —NMe), 2.53 (3H, s, —NHMe), 2.27 (4H, s, succinic acid); m/z (CI) 323 (M++1). (Found: C, 51.84; H, 6.19; N, 12.52. $C_{15}H_{22}N_4O_2Sx$ 1.0 $C_4H_6O_4$ requires: C, 51.80; H, 6.41; N, 12.72%).

EXAMPLE 16

3-(2-Aminoethyl)-5-[(1,1-dioxo-6-methyl-3,4,5,6-tetrahydro-1,2,6-thiadiazin-2-yl)methyl]-1H-indole 1.
3-[2-(N-Tert-butyloxycarbonylamino)ethyl]-5-[(1,1-dioxo-1,2,6-thiadiazin-2-yl)methyl]-1H-indole The title compound was prepared in 38% isolated yield from Intermediate 1 and 1,2,6-thiadiazine-1,1-dioxide (J. Org. Chem., 1982, 47, 536) using a similar method to that described for Example 1 (Method A, step 1). White foam; $\delta_H$ (250 MHz, $CDCl_3$) 8.20 (1H, br s, indole N—H), 7.90 (1H, dd, J=4.5 and 2.5 Hz, —CH—), 7.60 (1H, s, Ar—H), 7.40 (1H, d, J=8.5 Hz, Ar—H), 7.22 (1H, dd, J=8.5 and 1.7 Hz, Ar—H), 7.13 (1H, dd, J=7.3 and 2.5 Hz, —CH—), 7.10 (1H, d, J=2.1 Hz, Ar—H), 5.73 (1H, dd, J=7.3 and 4.5 Hz, —CH—), 5.05 (2H, s, Ar—$CH_2N$—), 4.60 (1H, br s, —NH—), 3.44 (2H, m, Ar—$CH_2CH_2N$—), 2.95 (2H, t, J=7.0 Hz, Ar—$CH_2$—), 1.43 (9H, s, t-Bu); m/z (FAB) 405 (M++1).

2.3-[2-(N-Tert-butyloxycarbonylamino)ethyl]-5-[(1,1-dioxo-6-methyl-3,4,5,6-tetrahydro-1,2,6-thiadiazin-2-yl)methyl]-1H-indole.

To a stirred solution of 2-methyl-3,4,5,6-tetrahydro-1,2,6-thiadiazine-1,1-dioxide (300 mg, 2.0 mmol) in anhydrous dimethylformamide (10 ml) was added sodium hydride (60% dispersion in oil; 71 mg) and the mixture was stirred under nitrogen for 20 minutes. A solution of the product from step 1 (300 mg, 0.74 mmol) in anhydrous dimethylformamide (5 ml) was added dropwise via cannula over 5 minutes to the above solution and the mixture was heated at 90°-100° C. for 45 minutes. After being cooled to room temperature, the mixture was diluted with water (50 ml) and extracted with ethyl acetate (2×100 ml). The combined organic solutions were washed with brine (1×50 ml), dried (MgSO$_4$) and concentrated. Flash chromatography (silica gel, diethyl ether) of the residue gave 100 mg (32%) of the required title compound; δ$_H$ (250 MHz, CDCl$_3$) 8.15 (1H, br s, indole N—H), 7.51 (1H, s, Ar—H), 7.35 (1H, d, J=8.5 Hz, Ar—H), 7.21 (1H, dd, J=8.5 and 1.5 Hz, Ar—H), 7.05 (1H, d, J=2.1 Hz, Ar—H), 4.60 (1H, br s, —NH—), 4.36 (2H, s, Ar—CH$_2$N—), 3.45 (2H, br q, J=6.9 Hz, —CH$_2$NH—), 3.38 (2H, t, J=5.7 Hz, —CH$_2$N—), 3.26 (2H, t, J=5.8 Hz, —CH$_2$N—), 2.94 (2H, t, J=6.9 Hz, ArCH$_2$CH$_2$NH—), 2.86 (3H, s, —NMe), 1.80—1.70 (2H, m, —CH$_2$—), 1.43 (9H, s, t-Bu).

3.
3-(2-Aminoethyl)-5-[(1,1-dioxo-6-methyl-3,4,5,6-tetrahydro-1,2,6-thiadiazin-2-yl)methyl]-1H-indole To a stirred solution of the product from step 2 (95 mg, 0.225 mmol) in anhydrous dichloromethane (5 ml) was added dropwise, under nitrogen, iodotrimethylsilane (35 μl). After being stirred at room temperature for 12 minutes the reaction was quenched with methanol (1 ml), solvents were removed under vacuum and the residue was purified by flash chromatography (silica gel, dichloromethane-methanol-ammonia 80:20:2) to give 44 mg (61%) of the title compound; δ$_H$ (250 MHz, CDCl$_3$) 8.21 (1H, br s, indole N—H), 7.52 (1H, s, Ar—H), 7.33 (1H, d, J=8.3 Hz, Ar—H), 7.18 (1H, d, J=8.3 Hz, Ar—H), 7.05 (1H, br s, Ar—H), 4.35 (2H, s, Ar—CH$_2$N—), 3.37 (2H, t, J=5.8 Hz, —CH$_2$N—), 3.25 (2H, t, J=5.6 Hz, —CH$_2$N—), 3.02 (2H, m, —CH$_2$—), 2.91 (2H, m, ArCH$_2$CH$_2$NH$_2$), 2.85 (3H, s, —NMe), 1.74 (2H, m, —CH$_2$—); m/z (CI) 323 (M$^+$+1).

EXAMPLE 17

3-[2-(Dimethylamino)ethyl]-5-[(1,1-dioxo-6-methyl-3,4,5,6-tetrahydro-1,2,6-thiadiazin-2-yl)methyl]-1H-indole. Oxalate The title compound was prepared in 77% yield from 3-(2-aminoethyl)-5-[(1,1-dioxo-6-methyl-3,4,5,6-tetrahydro-1,2,6-thiadiazin-2-yl)methyl]-1H-indole (Example 16) following the conditions described for Example 2. The oxalate salt was prepared and recrystallised from ethanol-diethyl ether; mp 190°-191° C.; δ$_H$ (360 MHz, D$_2$O) 7.64 (1H, s, Ar—H), 7.52 (1H, d, J=8.4 Hz, Ar—H), 7.35 (1H, s, Ar—H), 7.27 (1H, dd, J=8.4 and 1.5 Hz, Ar—H), 4.38 (2H, s, Ar—CH$_2$N—), 3.48 (2H, t, J=7.3 Hz, —CH$_2$NMe$_2$), 3.42 (2H, t, J=5.9 Hz, —CH$_2$N—), 3.33 (2H, t, J=5.7 Hz, —CH$_2$N—), 3.24 (2H, t, J=7.3 Hz, Ar—CH$_2$CH$_2$N—), 2.91 (6H, s, —NMe$_2$), 2.84 (3H, s, —NMe), 1.84 (2H, qn, J=5.8 Hz, —CH$_2$—); m/z (EI) 350 (M$^+$). Found: C, 51.80; H, 6.20; N, 12.06. C$_{17}$H$_{26}$N$_4$O$_2$S×1.05 C$_2$H$_2$O$_4$×0.2 C$_2$H$_6$O requires: C, 51.56; H, 6.50; N, 12.33%).

EXAMPLE 18

3-(2-Aminoethyl)-5-[(4,4-dimethyl-1,1-dioxo-1,2,5-thiadiazolidin-2-yl)methyl]-1H-indole 1. 3,3-Dimethyl-1,2,5-thiadiazolidine-1,1-dioxide To a refluxing solution of sulfamide (27.25 g, 283 mmol) in anhydrous pyridine (300 ml) was added dropwise 1,2-diamino-2-methylpropane (25 g, 283 mmol) over 2 hours. The resulting mixture was refluxed for further 16 hours under nitrogen before the solvent was removed under vacuum. The residue was triturated with hexane and the solid was collected by filtration and purified by flash chromatography (silica gel, dichloromethane-methanol 96:4) to give 36.1 g (85%) of the title compound as a white solid; mp 80°-83° C.; δ$_H$ (360 MHz, DMSO-d$_6$) 7.08 (1H, br t, —NH—), 6.77 (1H, s, —NH—), 3.04 (2H, d, J=6.9 Hz, —CH$_2$—), 1.24 (6H, s, —CMe$_2$); m/z (EI) 151 (M$^+$+1).

2.
3-[2-(N-Tert-butyloxycarbonylamino)ethyl]-5-[(4,4-dimethyl-1,1-dioxo-1,2,5-thiadiazolidin-2-yl)methyl]-1H-indole To a stirred solution of 3,3-dimethyl-1,2,5-thiadiazolidine-1,1-dioxide (360 mg, 2.4 mmol) in anhydrous dimethylformamide (10 ml) was added sodium hydride (60% dispersion in oil; 87 mg) and the mixture was stirred at room temperature for 30 minutes under nitrogen. A solution of Intermediate 3 (500 mg, 1.09 mmol) in anhydrous dimethylformamide (5 ml) was added to the above mixture and it was heated at 100° C. for 40 minutes. Solvents were removed under vacuum, the residue was diluted with water (50 ml) and products were extracted with diethyl ether (2×75 ml). The combined organic phases were washed with brine (1××40 ml), dried (MgSO$_4$) and concentrated. Flash chromatography of the residue (silica gel, diethyl ether) gave 334 mg (73%) of the required title compound; δ$_H$ (250 MHz, CDCl$_3$) 8.07 (1H, br, s, indole N—H), 7.55 (1H, s, Ar—H), 7.36 (1H, d, J=8.3 Hz, Ar—H), 7.22 (1H, dd, J=8.3 and 1.4 Hz, Ar—H), 7.06 (1H, d, J=2.0 Hz, Ar—H), 4.60 (1H, br s,—NHBOC), 4.28 (2H, s, Ar—CH$_2$N—), 4.14 (1H, br s, —NH—), 3.45 (2H, q, J=6.9 Hz, —CH$_2$NHBOC), 3.02 (2H, s, —CH$_2$—), 2.95 (2H, t, J=6.9 Hz, Ar—CH$_2$—), 1.43 (9H, s, t-Bu), 1.37 (6H, s, —CMe$_2$).

3.
3-(2-Aminoethyl)-5-[(4,4-dimethyl-1,1-dioxo-1,2,5-thiadiazolidin-2-yl)methyl]-1H-indole The title compound was prepared from the product from step 2 using the conditions described for Example 1 (step 2); colourless thick oil; δ$_H$ (360 MHz, CDCl$_3$) 8.09 (1H, br s, indole N—H), 7.58 (1H, s, Ar—H), 7.35 (1H, d, J=8.4 Hz, Ar—H), 7.21 (1H, dd, J=8.4 and 1.5 Hz, Ar—H), 7.08 (1H, d, J=2.1 Hz, Ar—H), 4.27 (2H, s, Ar—CH$_2$N—), 3.03 (2H, t, J=6.6 Hz, —CH$_2$NH$_2$), 3.01 (2H, s, —CH$_2$—), 2.90 (2H, t, J=6.6 Hz, Ar—CH$_2$—), 1.36 (6H, s, —CMe$_2$).

EXAMPLE 19

3-(2-Aminoethyl)-5-[(3,3-dimethyl-1,1-dioxo-1,2,5-thiadiazolidin-2-yl)methyl]-1H-indole 1.
2-Tert-butyloxycarbonyl-4,4-dimethyl-1,2,5-thiadiazolidine-1,1-dioxide To a stirred solution of 3,3-dimethyl-1,2,5-thiadiazolidine-1,1-dioxide (2.5 g, 16.6 mmol) in anhydrous dimethylformamide (50 ml) was added sodium hydride (60% dispersion in oil; 666 mg) in two portions. After being stirred at 40° C. for 50 minutes under nitrogen, the mixture was allowed to cool to room temperature, diluted with anhydrous dimethylformamide (20 ml) and treated with di-tert-butyldicarbonate (3.99 g, 18.26 mmol). After 1 hour 45 minutes of stirring at room temperature, the mixture was diluted with water (200 ml) and extracted with diethyl ether (3×100 ml). The organic phases were washed with brine (2×50 ml), dried (MgSO$_4$) and concentrated. Flash chromatography of the residue (silica gel, dichloromethane to dichloromethane-diethyl ether 50:50) gave a mixture of the required product and 2,5-di-tert-butyloxycarbonyl-3,3-dimethyl-1,2,5-thiadiazolidine-1,1-dioxide. Trituration of this mixture with hot hexane afforded 1.26 g (30%) of the required title compound as a white solid; $\delta_H$ (250 MHz, CDCl$_3$) 4.39 (1H, br s, —NH—), 3.70 (2H, s, —CH$_2$—), 1.54 (9H, s, t-Bu), 1.47 (6H, s, —CMe$_2$); m/z (CI) 249 (M$^+$ − 1).

2.
3-[2-(N-Tert-butyloxycarbonylamino)ethyl]-5-[(2-tert-butyloxycarbonyl-4,4-dimethyl-1,2,5-thiadiazolidin-5-yl)methyl]-1H-indole The title compound was prepared in 84% yield from Intermediate 3 and 2-tert-butyloxycarbonyl-4,4-dimethyl-1,2,5-thiadiazolidine-1,1-dioxide using a similar method to that described for Example 18 (step 2); white foam; $\delta_H$ (250 MHz, CDCl$_3$) 8.04 (1H, br s, indole N—H), 7.58 (1H, s, Ar—H), 7.32 (2H, s, Ar—H), 7.02 (1H, d, J=2.2 Hz, Ar—H), 4.59 (1H, br s, —NH—), 4.36 (2H, s, Ar—CH$_2$N—), 3.59 (2H, s, —CH$_2$—), 3.45 (2H, br q, J=6.3 Hz, —CH$_2$NH—), 2.94 (2H, t, J=6.3 Hz, Ar—CH$_2$—), 1.55 (9H, s, t-Bu), 1.43 (9H, s, t-Bu), 1.30 (6H, s, —CMe$_2$); m/z (FAB) 523 (M$^+$ + 1).

3.
3-(2-Aminoethyl)-5-[(3,3-dimethyl-1,1,-dioxo-1,2,5-thiadiazolidin-2-yl)methyl]-1H-indole A solution of the product from step 2 (450 mg) in 90% formic acid (18 ml) was stirred at room temperature for 1 hour and at 40° C. for 1 hour 20 minutes. The solvent was removed under vacuum and the residue was purified by flash chromatography (silica gel, dichloromethane-methanol-ammonia 80:20:2) to give 175 mg (63%) of the title compound as a colourless thick oil; $\delta_H$(360 MHz, CDCl$_3$) 8.04 (1H, br, s, indole N—H), 7.61 (1H, s, Ar—H), 7.32 (1H, d, J=8.3 Hz, Ar—H), 7.28 (1H, dd, J=8.3 and 1.4 Hz, Ar—H), 7.04 (1H, s, Ar—H), 4.37 (2H, s, Ar—CH$_2$N—), 3.26 (2H, s, —CH$_2$—), 3.01 (2H, t, J=6.6 Hz, —CH$_2$NH$_2$), 2.90 (2H, t, J=6.6 Hz, Ar—CH$_2$—), 1.22 (6H, s, —CMe$_2$); m/z (CI) 323 (M$^+$ + 1).

EXAMPLE 20

3-(2-Aminoethyl)-5-(1,1-dioxo-5-methyl-1,2,5-thiadiazolidin-2-yl)-1H-indole 1.
4-(1,1-dioxo-5-methyl-1,2,5-thiadiazolidine-2-yl)nitrobenzene To a solution of 2-methyl-1,2,5-thiadiazolidine-1,1-dioxide (2.02 g, 14.8 mmol) in anhydrous dimethylformamide (30 ml) was added sodium hydride (60% dispersion in oil; 0.59 g) and the mixture was stirred at room temperature under nitrogen for 40 minutes. A solution of 1-fluoro-4-nitrobenzene (2.09 g, 14.8 mmol) in anhydrous dimethylformamide (15 ml) was added to the above solution and the mixture was refluxed for 1 hour. Water (200 ml) was added and products were extracted with ethyl acetate (2×150 ml), dried (MgSO$_4$) and concentrated to an orange solid. Crystallisation from ethyl acetate (150 ml) afforded 2.61 g (68.7%) of the title compound as a pale orange solid; mp 155°-163° C.; $\delta_H$ (250 MHz, DMSO-d$_6$) 8.29 (2H, d, J=9.3 Hz, Ar—H), 7.34 (2H, d, J=9.3 Hz, Ar—H), 4.00 (2H, t, J=6.4 Hz, —CH$_2$—), 3.57 (2H, t, J=6.4 Hz, —CH$_2$—), 2.78 (3H, s, —CH$_3$); m/z (EI) 257 (M$^+$).

2.
4-(1,1-dioxo-5-methyl-1,2,5-thiadiazolidin-2-yl)aniline hydrochloride

A suspension of the previous compound (2.56 g) in a mixture of ethanol (80 ml), ethyl acetate (40 ml) and 2N hydrochloric acid (5.22 ml) was hydrogenated at 30 psi over 10% palladium on carbon (0.25 g) for 45 minutes. The catalyst was filtered off, washed with absolute ethanol and solvents were removed under vacuum to give a crude product (0.64 g) which was dissolved in water (100 ml) and washed with diethyl ether (2×50 ml) to eliminate a less polar impurity. Further washings of the catalyst with water (100 ml) afforded extra pure title compound which was combined with the previous aqueous phase and concentrated to give a combined yield of 2.43 g (92.6%) as a pale purple solid; $\delta_H$ (250 MHz, D$_2$O) 7.42 (4H, m, Ar—H), 3.96 (2H, t, J=6.3 Hz, —CH$_2$—), 3.60 (2H, t, J=6.3 Hz, —CH$_2$—), 2.86 (3H, s, —CH$_3$); m/z (EI) 227 (M$^+$).

3.
4-(1,1-dioxo-5-methyl-1,2,5-thiadiazolidin-2-yl)phenylhydrazine hydrochloride The title compound was prepared in 96% yield from 4-(1,1-dioxo-5-methyl-1,2,5-thiadiazolidin-2-yl)aniline hydrochloride using a similar method to that described for Intermediate 1 (step 1); yellow solid; $\delta_H$ (360 MHz, DMSO-d$_6$) 7.15 (2H, d, J=8.9 Hz, Ar—H), 6.92 (2H, d, J=8.9 Hz, Ar—H), 3.74 (2H, t, J=6.4 Hz, —CH$_2$—), 3.42 (2H, t, J=6.4 Hz, —CH$_2$—), 2.68 (3H, s, —CH$_3$); m/z (FAB) 243 (M$^+$ + 1).

4.
3-(2-Aminoethyl)-5-(1,1-dioxo-5-methyl-1,2,5-thiadiazolidin-2-yl)-1H-indole

A solution of the previous hydrazine hydrochloride (1.45 g, 4.95 mmol) and 4-chlorobutanal dimethylacetal (0.75 g, 4.95 mmol) in a mixture of absolute ethanol (50 ml) and water (10 ml) was refluxed under nitrogen for 3 hours. Solvents were removed under vacuum and the residue was purified by flash chromatography (silica gel, dichloromethane-methanol-ammonia 60:8:1 to 40:8:1) to give 159 mg (11%) of the title compound as a thick oil; $\delta_H$(360 MHz, DMSO-d$_6$) 10.9 (1 h, br s, indole N-H), 7.41 (1H, d, J=2.1 Hz, Ar—H), 7.35 (1H, d, J=8.5 Hz, Ar—H), 7.19 (1H, s, Ar—H), 7.08 (1H, dd, J=8.5 and 2.1 Hz, Ar—H), 3.84 (2H, t, J=6.3 Hz, —CH$_2$—), 3.44 (2H, t, J=6.3 Hz, —CH$_2$—), 2.88—2.74 (4H, m, —CH$_2$CH$_2$NH$_2$), 2.72 (3H, s, —NMe).

EXAMPLE 21

3-(2-Aminoethyl)-5-(5-benzyl-1,1-dioxo-1,2,5-thiadiazolidin-2-yl)-1H-indole 1. 2-Benzyl-1,2,5-thiadiazolidine-1,1-dioxide To a refluxing solution of sulfamide (27.12 g, 282 mmol) in anhydrous pyridine (250 ml) was added dropwise N-benzylethylenediamine (42.4 ml, 282 mmol)

over 3 hours. The resulting solution was refluxed under nitrogen for a further 16 hours before the solvent was removed under vacuum. The residue was dissolved in dichloromethane (100 ml) and washed with 2N hydrochloric acid (1×100 ml). The aqueous layer was extracted with dichloromethane (2×100 ml) and the combined organic solutions were washed with brine (50 ml), dried (Na$_2$SO$_4$) and concentrated. Flash chromatography of the residue (silica gel, dichloromethane-methanol 95:5) gave 47.3 g (79%) of the title compound as a white solid; $\delta_H$(360 MHz, CDCl$_3$) 7.32 (5H, m, Ph), 4.34 (1H, br s, —NH—), 4.18 (2H, s, Ar—CH$_2$N—), 3.47 (2H, q, J= 6.4 Hz,—CH$_2$NH—),3.27(2H, t, J=6.4 Hz,—CH$_2$—); m/z (CI) 2$\overline{13}$ (M$^+$ +1).

2.
4-(5-Benzyl-1,1-dioxo-1,2,5-thiadiazolidin-2-yl)nitrobenzene

The title compound was prepared in 79% yield from 2-benzyl-1,2,5-thiadiazolidine-1,1-dioxide and 1-fluoro-4-nitrobenzene using a similar method to that described for Example 20 (step 1). The crude product was crystallised from ethyl acetate to give a yellow solid; mp 164°-165° C.; $\delta_H$ (360 MHz, DMSO-d$_6$) 8.30 (2H, d, J=9.2 Hz, Ar—H), 7.40 (5H, m, Ph), 7.33 (2H, d, J=9.2 Hz, Ar—H), 4.31 (2H, s, PhC$\underline{H}_2$—), 3.98 (2H, t, J=6.4 Hz, —CH$_2$—), 3.49 (2H, t, J=6.4 Hz, —CH$_2$—); m/z (EI) 333 (M$^+$).

3.
4-(5-Benzyl-1,1-dioxo-1,2,5-thiadiazolidin-2-yl)aniline hydrochloride A solution of the previous nitro compound (5.08 g) in a mixture of ethanol (20 ml), ethyl acetate (100 ml), water (8 ml) and 1N hydrochloric acid (16 ml) was hydrogenated at 30 psi over 10% palladium on carbon for 25 minutes. The catalyst was filtered off, washed with ethanol and water and solvents were removed under vacuum. The residue was crystallised from a mixture of ethanol (150 ml) and water (5 ml) to give 3.19 g (61%) of the title compound; $\delta_H$ (250 MHz, DMSO-d$_6$) 7.44—7.27 (9H, m, Ph and Ar—H), 4.25 (2H, s, PhC$\underline{H}_2$—), 3.83 (2H, t, J=6.4 Hz, —CH$_2$—), 3.42 (2H, t, J=6.4 Hz, —CH$_2$—).

4.
4-(5-Benzyl-1,1-dioxo-1,2,5-thiadiazolidin-2-yl)phenylhydrazine hydrochloride The title compound was prepared from 4-(5-benzyl-1,1-dioxo-1,2,5-thiadiazolidin-2-yl)aniline hydrochloride by a similar method to that described for Intermediate 1 (step 1); pale brown solid; $\delta_H$ (250 MHz, DMSO-d$_6$) 7.42-7.32 (5H, m, Ph), 7.24 (2H, d, J=8.5 Hz, Ar—H), 7.02 (2H, d, J=8.5 Hz, Ar—H), 4.24 (2H, s, PhC$\underline{H}_2$—), 3.68 (2H, t, J=6.4 Hz, —CH$_2$—), 3.39 (2H, t, J=6.4 Hz, —CH$_2$—).

5.
3-(2-Aminoethyl)-5-(5-benzyl-1,1-dioxo-1,2,5-thiadiazolidin-2-yl)-1H-indole The title compound was prepared in 8% yield from the previous hydrazine hydrochloride and 4-chlorobutanal dimethylacetal using the conditions described for Example 20 (step 4); brown solid; $\delta_H$ (250 MHz, DMSO-d$_6$) 10.91 (1H, br s, indole N—H), 7.45-7.33 (7H, m, Ph and Ar—H), 7.20 (1H, s, Ar—H), 7.12 (1H, dd, J=8.7 and 2.1 Hz, Ar—H), 4.24 (2H, s, PhC$\underline{H}_2$—), 3.84 (2H, t, J=6.3 Hz, —CH$_2$—), 3.37 (2H, t, J=6.3 Hz, —CH$_2$—), 2.80 (4H, m, —CH$_2$CH$_2$NH$_2$).

Examples 22 to 25 were prepared from the products of Examples 18 to 21 respectively using a similar method to that described for Example 2.

EXAMPLE 22
3-[2-(Dimethylamino)ethyl]-5-[(4,4-dimethyl-1,1-dioxo-1,2,5-thiadiazolidin-2-yl)methyl]-1H-indole. Succinate The succinate salt was prepared and recrystallised from ethanol-diethyl ether; mp 149°-151° C.; $\delta_H$ (360 MHz, DMSO-d$_6$) 10.85 (1H, s, indole N—H), 7.50 (1H, s, Ar—H), 7.32 (1H, d, J=8.3 Hz, Ar—H), 7.18 (1H, s, Ar—H), 7.06 (1H, dd, J=8.3 and 1.4 Hz, Ar—H), 4.10 (2H, s, Ar—CH$_2$N—), 2.93 (2H, s, —CH$_2$—), 2.87 (2H, t, J=8.5 Hz, —CH$_2$—), 2.71 (2H, t, J=8.5 Hz, —CH$_2$—), 2.37 (6H, s —NMe$_2$), 2.36 (4H, s, succinic acid), 1.23 (6H, s, —CMe$_2$); m/z (EI) 350 (M$^+$). (Found: C, 53.49; H, 6.55; N, 11.74. C$_{17}$H$_{26}$N$_4$O$_2$Sx 1.0 C$_4$H$_6$O$_4$ requires: C, 53.83; H, 6.88; N, 11.96%).

EXAMPLE 23
3-[2-(Dimethylamino)ethyl]-5-[(3,3-dimethyl-1,1-dioxo-1,2,5-thiadiazolidin-2-yl)methyl]-1H-indole. Succinate The succinate salt was prepared and recrystallised from ethanol-diethyl ether; mp 164°-166° C.; $\delta_H$ (360 MHz, DMSO-d$_6$) 10.76 (1H, br s, indole N—H), 7.52 (1H, s, Ar—H), 7.30-7.25 (2H, m, Ar—H and —NH—), 7.13 (1H, s, Ar—H), 7.12 (1H, d, J=8.5 Hz, Ar—H), 4.21 (2H, s, Ar—CH$_2$N—), 3.09 (2H, d, J=7.1 Hz, —CH$_2$—), 2.83 (2H, t, J=8.4 Hz, —CH$_2$—), 2.65 (2H, t, J=8.4 Hz, —CH$_2$—), 2.34 (2H, s, succinic acid), 2.32 (6H, s, —NMe$_2$), 1.14 (6H, s, —CMe$_2$); m/z (CI) 351 (M$^+$+1). (Found: C, 55.89; H, 6.92; N, 13.59. C$_{17}$H$_{26}$N$_4$O$_2$Sx 0.5 C$_4$H$_6$O$_4$ requires: C, 55.72; H, 7.14; N, 13.68%).

EXAMPLE 24
3-[2-(Dimethylamino)ethyl]-5-(1,1-dioxo-5-methyl-1,2,5-thiadiazolidin-2-yl)-1H-indole. Oxalate The oxalate salt was prepared and recrystallised from methanol-diethyl ether; mp 169°-176° C.; $\delta_H$(360 MHz, D$_2$O) 7.62 (1H, d, J=2.0 Hz, Ar—H), 7.58 (1H, d, J=8.7 Hz, Ar—H), 7.38 (1H, s, Ar—H), 7.26 (1H, dd, J=8.7 and 2.1 Hz, Ar—H), 3.95 (2H, t, J=6.3 Hz, —CH$_2$—), 3.59 (2H, t, J=6.3 Hz, —CH$_2$—), 3.46 (2H, t, J=7.4 Hz, —CH$_2$—), 3.20 (2H, t, J=7.4 Hz, —CH$_2$—), 2.90 (6H, s, —NMe$_2$), 2.86 (3H, s, —CH$_3$); m/z (CI) 323 (M$^+$+1). (Found: C, 48.60; H, 5.73; N, 13.37. C$_{15}$H$_{22}$N$_4$O$_2$Sx 1.0 C$_2$H$_2$O$_4$x 0.3 H$_2$O requires: C, 48.86; H, 5.93; N, 13.41%).

EXAMPLE 25
3-[2-(Dimethylamino)ethyl]-5-(5-benzyl-1,1-dioxo-1,2,5-thiadiazolidin-2-yl)-1H-indole. Oxalate The oxalate salt was prepared and recrystallised from methanol; mp 157°-165° C.; $\delta_H$ (360 MHz, DMSO-d$_6$) 11.09 (1H, br s, indole N—H), 7.51 (1H, s, Ar—H), 7.45-7.32 (6H, m, Ph and Ar— H), 7.30 (1H, s, Ar—H), 7.18 (1H, dd, J=8.0 and 1.4 Hz, Ar—H), 4.24 (2H, s, PhCH$_2$—), 3.86 (2H, t, J=6.3 Hz, —CH$_2$—), 3.38 (2H, t, J=6.3 Hz, —CH$_2$—), 3.26 (2H, m, —CH$_2$—), 3.05 (2H, m, —CH$_2$—), 2.80 (6H, s, —NMe$_2$); m/z (EI) 398 (M$^+$). (Found: C, 55.32; H, 5.87; N, 11.05. C$_{21}$H$_{26}$N$_4$O$_2$Sx 1.0C$_2$H$_2$O$_4$x 0.6H$_2$O requires: C, 55.32; H, 5.89; N, 11.22%).

EXAMPLE 26

Tablet Preparation

Tablets containing 1.0, 2.0, 25.0, 26.0, 50.0 and 100.0 mg, respectively of the following compounds are prepared as illustrated below:

3-[2-(Dimethylamino)ethyl]-5-[(1,1-dioxo-5-methyl-1,2,5-thiadiazolidin-2-yl)methyl]-1H-indole. Succinate 3-[2-(Dimethylamino)ethyl]-5-[(1,1-dioxo-6-methyl-3,4,5,6-tetrahydro-1,2,6-thiadiazin-2-yl)methyl]-1H-indole. Oxalate

| TABLE FOR DOSES CONTAINING FROM 1-25 MG OF THE ACTIVE COMPOUND | | | |
|---|---|---|---|
| | Amount-mg | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26-100 MG OF THE ACTIVE COMPOUND | | | |
|---|---|---|---|
| | Amount-mg | | |
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active ingredient per tablet.

What is claimed is:

1. A compound of formula I or pharmaceutically acceptable salt thereof:

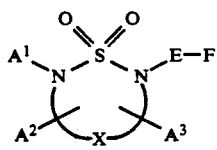

wherein

—X— represents —$(CH_2)_m$— in which m is 2 ;

$A^1$ represents hydrogen, hydrocarbon or a heterocyclic selected from the group consisting of $C_{3-7}$ heterocycloalkyl, $C_{3-7}$ heterocycloalkyl ($C_{1-6}$) alkyl, heteroaryl and heteroaryl ($C_{1-6}$) alkyl;

$A^2$ and $A^3$ independently represent hydrogen or $C_{1-6}$ alkyl;

E represents a bond or a straight or branched alkylene chain containing from 1 to 4 carbon atoms; and F represents a group of formula

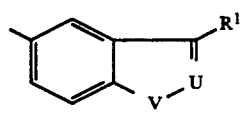

in which

U represents nitrogen or C—$R^2$;

V represents oxygen, sulphur or N—$R^3$ $R^1$ represents —$(CH_2)_pCHR^4.NR^6R^7$ or a group of formula

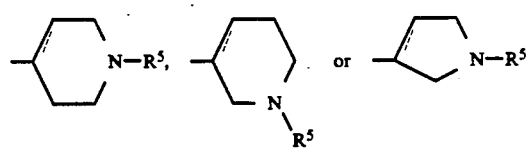

in which the broken line represents an optional chemical bond;

p is 1 or 2; and $R^2$, $R^3$, $R^4$, $R^5$, $R^6$ and $R^7$ independently represent hydrogen or $C_{1-6}$ alkyl.

2. A compound according to claim 1, wherein one of $A^2$ and $A^3$ represents hydrogen and the other represents hydrogen or $C_{1-6}$ alkyl.

3. A compound according to claim 1, wherein $R^1$ is selected from the group consisting of aminoethyl, N-methylaminoethyl, N,N-dimethylaminoethyl, 4-piperidyl, 1-methyl-4-piperidyl, 3-pyrrolidinyl and 1-methyl-3-pyrrolidinyl.

4. A compound according to claim 1 represented by formula IIA or pharmaceutically acceptable salt thereof:

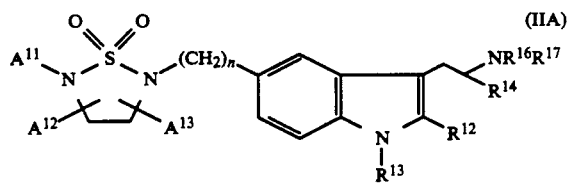

wherein n is zero, 1, 2 or 3;

$A^{11}$ represents hydrogen; or is selected from the group consisting of $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl and heteroaryl ($C_{1-6}$)alkyl, any of which groups may be optionally substituted with a substituent selected from the group consisting of trifluoromethyl, $C_{1-6}$ alkoxy, $C_{2-6}$ alkoxycarbonyl, $C_{2-6}$ alkylcarbonyl, $C_{1-6}$ alkylsulphonyl, arylsulphonyl, amino, mono- or di($C_{1-6}$)alkylamino, $C_{2-6}$ alkylcarbonylamino, arylcarbonylamino, $C_{2-6}$ alkoxycarbonylamino, $C_{1-6}$ alkylsulphonylamino, arylsulphonylamino, $C_{1-6}$ alkylsulphonylaminomethyl, aminocarbonylamino, mono- or di($C_{1-6}$)alkylaminocarbonylamino, mono- or diarylaminocarbonylamino, pyrrolidylcarbonylamino, aminocarbonyl, mono- or di($C_{1-6}$)alkylaminocarbonyl, $C_{1-6}$ alkylaminosulphonyl, aminosulphonylmethyl and mono-or di($C_{1-6}$)alkylaminosulphonylmethyl; and $A^{12}$, $A^{13}$, $R^{12}$, $R^{13}$, $R^{14}$, $R^{16}$ and $R^{17}$ independently represent hydrogen or $C_{1-6}$ alkyl.

5. A compound according to claim 4, wherein n is zero, 1 or 2.

6. The compound according to claim 1 selected from, the group consisting of

3-[2-(dimethylamino)ethyl]-5-[(1,1-dioxo-5-methyl-1,2,5-thiadiazolidin-2-yl)methyl]-1H-indole;

3-(2-aminoethyl)-5-[(1,1-dioxo-5-methyl-1,2,5-thiadiazolidin-2-yl)methyl]-1H-indole;
3-[2-(dimethylamino)ethyl]-5-[2-(1,1-dioxo-5-methyl-1,2,5-thiadiazolidin-2-yl)ethyl]-1H-indole;
3-(2-aminoethyl)-5-[2-(1,1-dioxo-5-methyl-1,2,5-thiadiazolidin-2yl)ethyl]-1H-indole;
3-[2-(dimethylamino)ethyl]-5-[(5-(4-acetylaminobenzyl)-1,1-dioxo-1,2,5-thiadiazolidin-2-yl)methyl]-1H-indole;
3-(2-aminoethyl)-5-[(5-(4-acetylaminobenzyl)-1,1-dioxo-1,2,5-thiadiazolidin-2-yl)methyl]-1H-indole;
3-(2-aminoethyl)-5-[(1,1-dioxo-1,2,5-thiadiazolidin-2-yl)methyl]-1H-indole;
3-(2-aminoethyl)-5-[(1,1-dioxo-5-isopropyl-1,2,5-thiadiazolidin-2-yl)methyl]-1H-indole;
3-(2-aminoethyl)-5-[2-(1,1-dioxo-1,2,5-thiadiazolidin-2-yl)ethyl]-1H-indole;
3-(2-aminoethyl)-5-[2-(1,1-dioxo-5-ethyl-1,2,5-thiadiazolidin-2-yl)ethyl]-1H-indole;
3-[2-(dimethylamino)ethyl]-5-[(1,1-dioxo-1,2,5-thiadiazolidin-2-yl)methyl]-1H-indole;
3-[2-(dimethylamino)ethyl]-5-[(1,1-dioxo-5-isopropyl-1,2,5-thiadiazolidin-2-yl)methyl]-1H-indole;
3-[2-(dimethylamino)ethyl]-5-[2-(1,1-dioxo-1,2,5-thiadiazolidin-2-yl)ethyl]-1H-indole;
3-[2-(dimethylamino)ethyl]-5-[2-(1,1-dioxo-5-ethyl-1,2,5-thiadiazolidin-2-yl)ethyl]-1H-indole;
3-[2-(methylamino)ethyl]-5-[(1,1-dioxo-5-methyl-1,2,5-thiadiazolidin-2-yl)methyl]-1H-indole;
3-(2-aminoethyl)-5-[(4,4-dimethyl-1,1-dioxo-1,2,5-thiadiazolidin-2-yl)methyl]-1H-indole;
3-(2-aminoethyl)-5-[(3,3-dimethyl-1,1-dioxo-1,2,5-thiadiazolidin-2-yl)methyl]-1H-indole;
3-(2-aminoethyl)-5-(1,1-dioxo-5-methyl-1,2,5-thiadiazolidin-2-yl)-1H-indole;
3-(2-aminoethyl)-5-(5-benzyl-1,1-dioxo-1,2,5-thiadiazolidin-2-yl)-1H-indole;
3-[2-(dimethylamino)ethyl]-5-[(4,4-dimethyl-1,1-dioxo-1,2,5-thiadiazolidin-2-yl)methyl]-1H-indole;
3-[2-(dimethylamino)ethyl]-5-[(3,3-dimethyl-1,1-dioxo-1,2,5-thiadiazolidin-2-yl)methyl]-1H-indole;
3-[2-(dimethylamino)ethyl]-5-(1,1-dioxo-5-methyl-1,2,5-thiadiazolidin-2-yl)-1H-indole;
3-[2-(dimethylamino)ethyl]-5-(5-benzyl-1,1-dioxo-1,2,5-thiadiazolidin-2-yl)-1H-indole;
or pharmaceutically acceptable salt thereof.

7. A pharmaceutical composition comprising an effective amount of a compound according to claim 1 in association with a pharmaceutically acceptable carrier or excipient.

8. A method for the treatment of migraine and associated conditions, said method comprises administering to a patient in need of such treatment an effective amount of a compound according to claim 1.

* * * * *